United States Patent [19]

Al Marachy et al.

[11] 4,079,393

[45] Mar. 14, 1978

[54] BLOOD TYPING INSTALLATIONS

[76] Inventors: Pierre Fauzy Al Marachy, 54 rue Boissonnade, 75014 Paris, France; Romain Gabriel Robuchon-Merovak, 36 rue Marius Aufan, 92300 Levallois-Perret, France; Christian Romain Robuchon-Merovak, 21 Cite Dupont, 75011 Paris, France

[21] Appl. No.: 646,540

[22] Filed: Jan. 5, 1976

[30] Foreign Application Priority Data

| Jan. 1, 1975 | France | 75 00245 |
| May 20, 1975 | Switzerland | 006469/75 |
| Nov. 27, 1975 | Switzerland | 015404/75 |
| Nov. 27, 1975 | Switzerland | 015405/75 |

[51] Int. Cl.² ............................................. G03B 15/00
[52] U.S. Cl. ........................................ 354/77; 354/81; 354/109; 356/39
[58] Field of Search ............... 354/80, 81, 76, 105, 354/109, 77, 78; 128/2 G; 356/39; 346/107 R

[56] References Cited

U.S. PATENT DOCUMENTS

| 2,339,657 | 1/1944 | Smith | 354/80 |
| 2,942,537 | 6/1960 | Zimmerman | 354/109 |
| 3,168,859 | 2/1965 | Mast | 354/105 X |
| 3,285,150 | 11/1966 | Wunderle | 354/105 X |
| 3,453,941 | 7/1969 | Marachy | 354/76 |
| 3,617,222 | 11/1971 | Matte | 356/39 X |

FOREIGN PATENT DOCUMENTS

| 2,432,086 | 1/1975 | Germany | 356/39 |
| 35,456 | 11/1967 | Japan | 355/77 |

Primary Examiner—Edna M. O'Connor
Attorney, Agent, or Firm—Roylance, Abrams, Berdo & Kaul

[57] ABSTRACT

A blood typing installation comprises a transparent cradle for a glass agglutination plate and a flash behind the cradle to project an image of the plate via an optical system onto a screen at the bottom of a laterally open box carried by sliding tubes mounted on the installation casing. Further sliding tubes carry a camera for photographing both the image on the screen and the individual whose blood is being typed and who is placed behind the box, to provide a record card.

43 Claims, 23 Drawing Figures

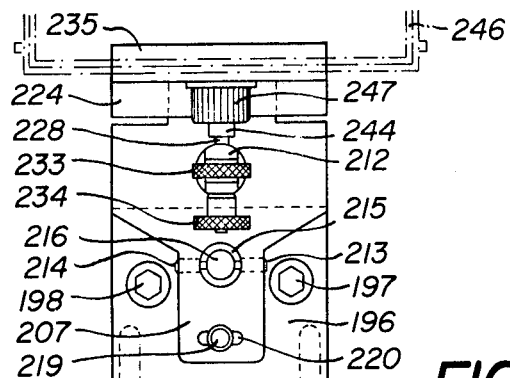
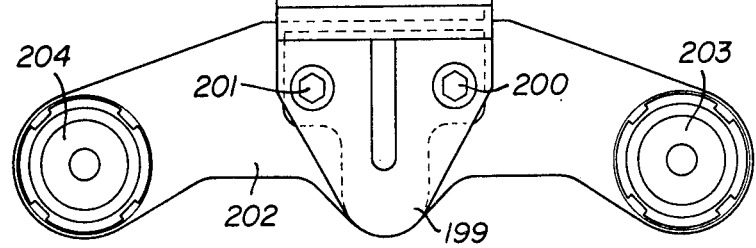
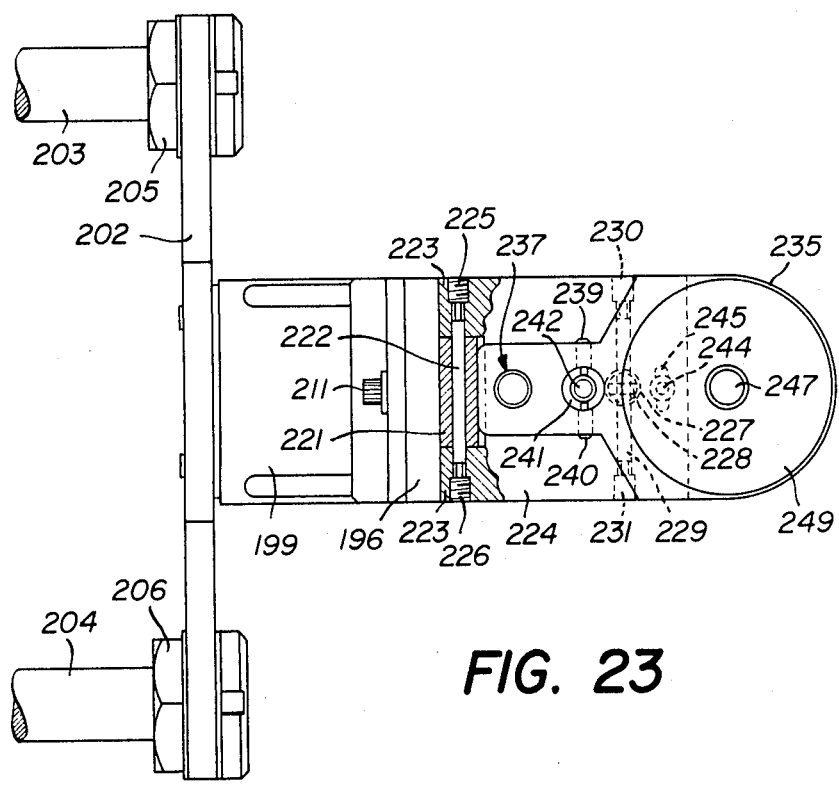
FIG. 22
FIG. 23

BLOOD TYPING INSTALLATIONS

The invention is concerned with the typing of an individual's blood.

To type an individual's blood one mixes samples of his blood with various test-sera, here anti-A, anti-B, anti-AB and anti-D, one deposits the different mixtures on a so-called agglutination plate, one examines the plate to see whether or not there has been any agglutination in the mixtures, one determines, on the basis of the results obtained, the blood group of the analysed blood, and one prepares a corresponding record card.

These operations can give rise to handling errors, errors in the interpretation of the results and/or errors of transcription. Now, such errors, as is known, can have grave consequences since they can be the cause of an individual's death in the event of a blood transfusion. It is therefore important to avoid them.

Thus, it has been proposed to design an installation which enables, firstly, the mixing and depositing operations to be carried out automatically and, secondly, in order to avoid having the results of one individual being attributed to another, the individual's portrait and the image of the agglutination plate to be recorded simultaneously with a camera after obtaining the results, as envisaged in particular in French Pat. No. 1,483,781. The construction contemplated in this specification gives rise to a number of problems. For instance, no satisfactory photographs could be obtained for various optical and lighting reasons.

The invention firstly provides an installation enabling an individual's blood to be typed and both his portrait and the typing results to be recorded with a camera, in a satisfactory manner.

The installation according to the invention comprises a plate holder for holding a transparent agglutination plate on which are deposited blob-forming mixtures of test-sera and of blood taken from the individual and letting light pass therethrough in the region occupied by the plate, a screen, an optical system between the plate holder and the screen, and a source of light behind the plate holder to project on to the screen, via the optical system, an image of the blobs formed by said mixtures on the plate, the camera being positioned in relation to the screen to simultaneously photograph the screen and the individual.

Preferably the screen is disposed at the bottom of a box that is open in the direction of the camera and that is provided with a protective cover to prevent the image projected by said light source from being cancelled out by a flash for lighting the individual triggered off by the camera.

Since only a specialist would be capable of interpreting the results obtained on the agglutination plate, it has moreover been proposed to dispose adjacent the latter an auxiliary plate bearing the information that is needed to enable a person without any special knowledge to identify the blood group of the individual whose blood has been analysed, to wit the conventional indication A, B, AB or O followed by the sign + or −, as the case may be, such auxiliary plate being photographed at the same time as the agglutination plate. It has also been proposed to cause the name of the individual and other possible information to appear in the photograph.

By providing this auxiliary blood-group-defining plate new possibilities for error are introduced since a laboratory assistant or other person will first have to interpret the results obtained on the agglutination plate and then select an auxiliary plate before placing the latter adjacent the plate.

The invention also provides means capable of being used in conjunction with an installation according to the invention for checking on a record card bearing, on the one hand, a reproduction of the results, enabling an individual's blood group and rhesus factor to be determined, obtained on an agglutination support, with mixtures of blood taken from the individual and of different appropriate test sera, and, on the other hand, a definition of said blood group in conventional A, B, AB or O form followed by the sign + or −, whether or not the definition corresponds to said results, by comparing said reproduction and said definition with corresponding reference data acknowledged as being correct, said means comprising a carrier on which are represented, by way of reference data, the various possible results that can be obtained on an agglutination support and, adjacent each representation, the corresponding conventional definition.

In a particular form of embodiment of said means the carrier is a rotary member mounted in a casing having a window in which only one set of reference data, consisting of one of said possible results and the corresponding conventional definition, may be displayed at the same time.

To perform the mixing operation, it has moreover been proposed to provide in the installation disclosed in French Pat. No. 1,483,781 four pipettes, i.e. one pipette per mixture, which are connected by tubes to a peristaltic pump and which each come to take up a set quantity of different test serum and then a set quantity of blood on a previously punctured finger of the individual whose blood is to be typed. The various test sera are contained in four bottles that are placed in the installation in a set order. Now, the placing of these bottles can give rise to errors and since the bottles should be put every evening in a refrigerator and then put back in the installation the following morning, the possibilities for making errors are at least daily, not counting the error possibilities that exist during each bottle refilling operation.

The invention further provides a bottle-holding device intended, in particular, to be used in conjunction with an installation according to the invention and capable of reducing these new error possibilities.

This device comprises a movable holder having a base on which the bottles are placed in a row in a set order and which is provided with dissymmetrical positioning means intended to cooperate with complementary dissymmetrical positioning means provided on a support on which the holder is placed to enable the bottles to be used.

In a particular form of embodiment of this bottle-holding device, the holder comprises two end walls at the end of the row, one end wall having manual screw clamping means for clamping the bottles against each other and against the other end wall. This enables the holder and the bottles to form a rigid unit, saving the bottles from dropping out of the holder during handling of the latter.

The invention further provides an adjustable mounting intended in particular to be secured to the frame of the installation according to the invention and to carry an object, such as a camera, that enables the position of the object to be accurately adjusted in relation to the member to which the mounting is secured in at least one plane.

The adjustable mounting according to the invention, in its broadest aspect, comprises screw adjustment means cooperating with the or each pair of elements to adjust the angular position thereof.

The invention moreover provides a pipette capable of being used in an installation according to the invention, said pipette comprising an elongated tubular body having at one end a portion of reduced internal diameter, and an imperfect valve member cooperating with said portion, such portion acting as a seat for the valve member. In a preferred embodiment, the valve member is a slotted fishing line sinker having an irregular outer surface.

In the accompanying drawings, given by way of example:

FIG. 22 is an end view of the mounting shown in FIG. 21; and

FIG. 23 is a plan view of the same mounting.

Figure 1:
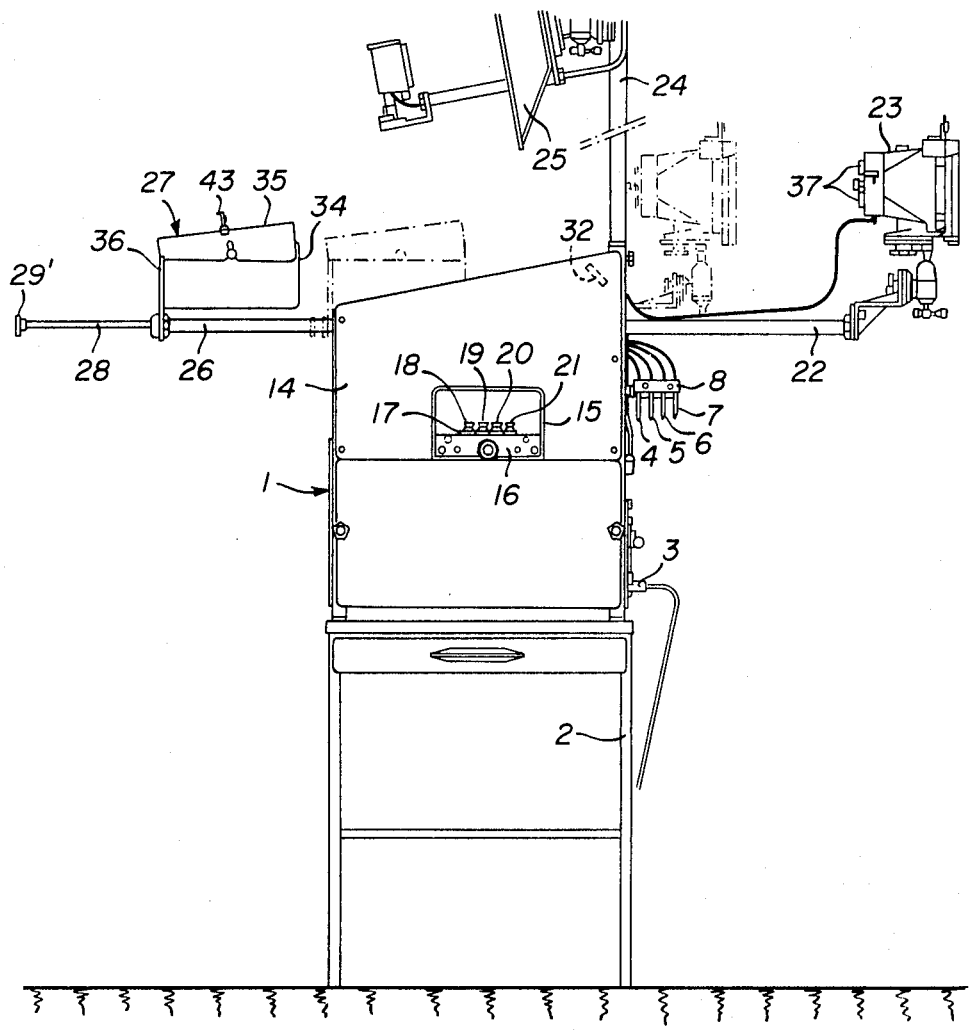
FIG. 1 is an overall side view of a blood typing installation according to the invention.

The installation shown in FIGS. 1 to 12 comprises a casing 1 supported by a table 2 and supplied with electric current via a socket 3. Four pipettes 4, 5, 6 and 7 are carried by a movable horizontal arm 8 and are connected to a peristaltic pump 9 (FIGS. 11 and 12) through flexible tubes 10, 11, 12 and 13.

The casing 1 has a side wall 14 in which is formed an opening 15 through which is inserted a drawer 16 (see also FIGS. 6 and 7) comprising a holder 17 for four bottles 18, 19, 20 and 21 respectively containing anti-A, anti-B, anti-AB and anti-D test serum. The movable arm 8 is so constructed as to rotate about a vertical axis and, in one of its angular positins (FIG. 7), it dips the lower ends of pipettes 4, 5, 6 and 7 respectively into the bottles 21, 20, 19 and 18, as will be explained later.

The casing 1 is fitted with two sliding tubes 22 supporting a camera 23, an upright sliding tube 24 supporting a light source 25 provided with a reflector, and two sliding tubes 26 supporting a box 27. The sliding tubes 26 contain each an internal sliding rod 28. The rods 28 have at their outer ends knobs or handles 29' for positioning an individual, whose blood is being typed, in relation to the camera 23.

The sliding members are intended firstly, to enable focussing adjustments to be made for photograph taking purposes and, secondly, to enable the installation to be put into compact form for transport purposes.

For photograph taking purposes, the individual is placed behind the box 27, in a sitting position on a stool of adjustable height. His position in relation to the installation is set by the knobs 29' of the sliding rods 28, extended to their outermost position. The individual holds the knobs 29' in his hands and his elbows alongside the body. The height of the stool is adjusted so that the individual's shoulders project above the box 27, and the light source 25 is arranged to illuminate him in a suitable manner. The image of an agglutination plate 29 and that of an auxiliary plate 30, both of transparent material, are projected through the intermediary of an optical system, comprising a lens unit 31 and a mirror 32, on to a screen 33 located at the bottom or end of the box 27 (FIG. 2), in such manner that the camera 23 may photograph at the same time the individual's portrait, the agglutination plate 29 and the auxiliary plate 30.

The box 27 is open on the side 34 directed towards the camera and comprises a protective lid 35 which pivots about an axis 36, in such manner as to enable the position of its front edge to be adjusted whereby the image of the agglutination plate 29 may occupy a precise position in relation to the individual's portrait. This adjustment is particularly necessary where the camera is required to take simultaneously several photographs by means of several lens units 37.

Figure 2:
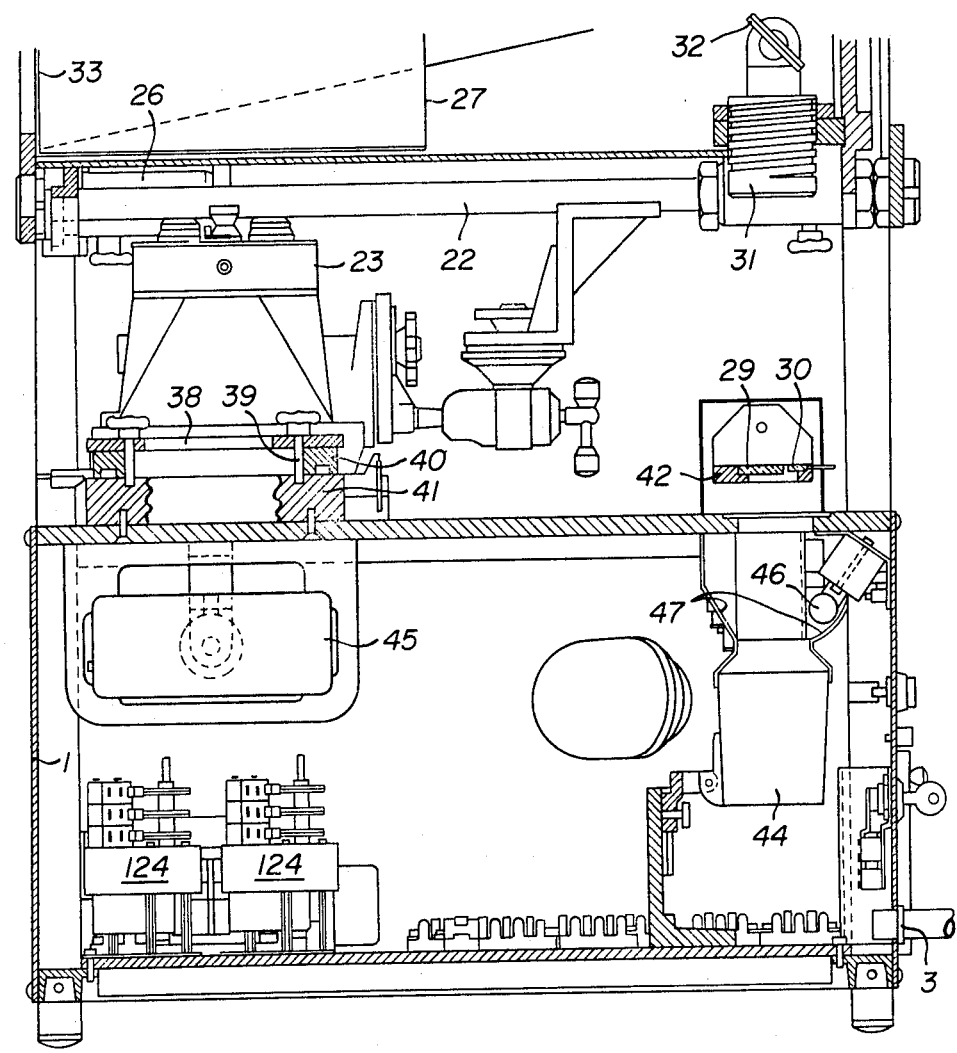
FIG. 2 is a side view, partly in section and on an enlarged scale, of part of the FIG. 1 installation, showing certain components in a packed away condition.

During transport of the installation, the various sliding members are pushed telescopically inside the casing 1 and the camera 23 is disposed inside the casing in a space provided for the purpose, visible in FIG. 2, where it is kept in place by a holding member 38 which clamps, with the aid of screws 39, the handle 40 of the camera on a base 41.

The agglutination plate 29 is placed on an apertured cradle 42. This cradle also comprises an open space for the auxiliary plate 30. The latter is provided with the conventional indication about the group of the analysed blood, to wit A, B, AB or O followed by the sign + or −, in such manner that there is simultaneously projected on to screen 33 the results obtained on the agglutination plate 29 and the conventional indication about the blood group as established by examination of the plate. Also, various items of information about the identity of the individual being photographed may be made to appear in the photograph, these items of information being placed on a supporting tablet 43 secured to the protective lid 35 of box 27.

When the photograph is being taken, the image of plate 29 and that of auxiliary plate 30 are projected on to screen 33 by an electronic flash 44, supplied in known manner by a storage battery 45. The light from the flash illuminates plate 29 and auxiliary plate 30 from the rear in such manner that the light beam will pass through the lens unit 31, and then on to the mirror 32 which reflects the image on to the screen 33.

To enable focussing of the optical system prior to the photograph being taken, there is provided in the installation a light source 46 cooperating with a reflector 47, this lighting being sufficient to project the images of the plates 29 and 30 on to the screen 33, whereby the focussing may be carried out by actuation of the lens unit 31.

Figure 3:
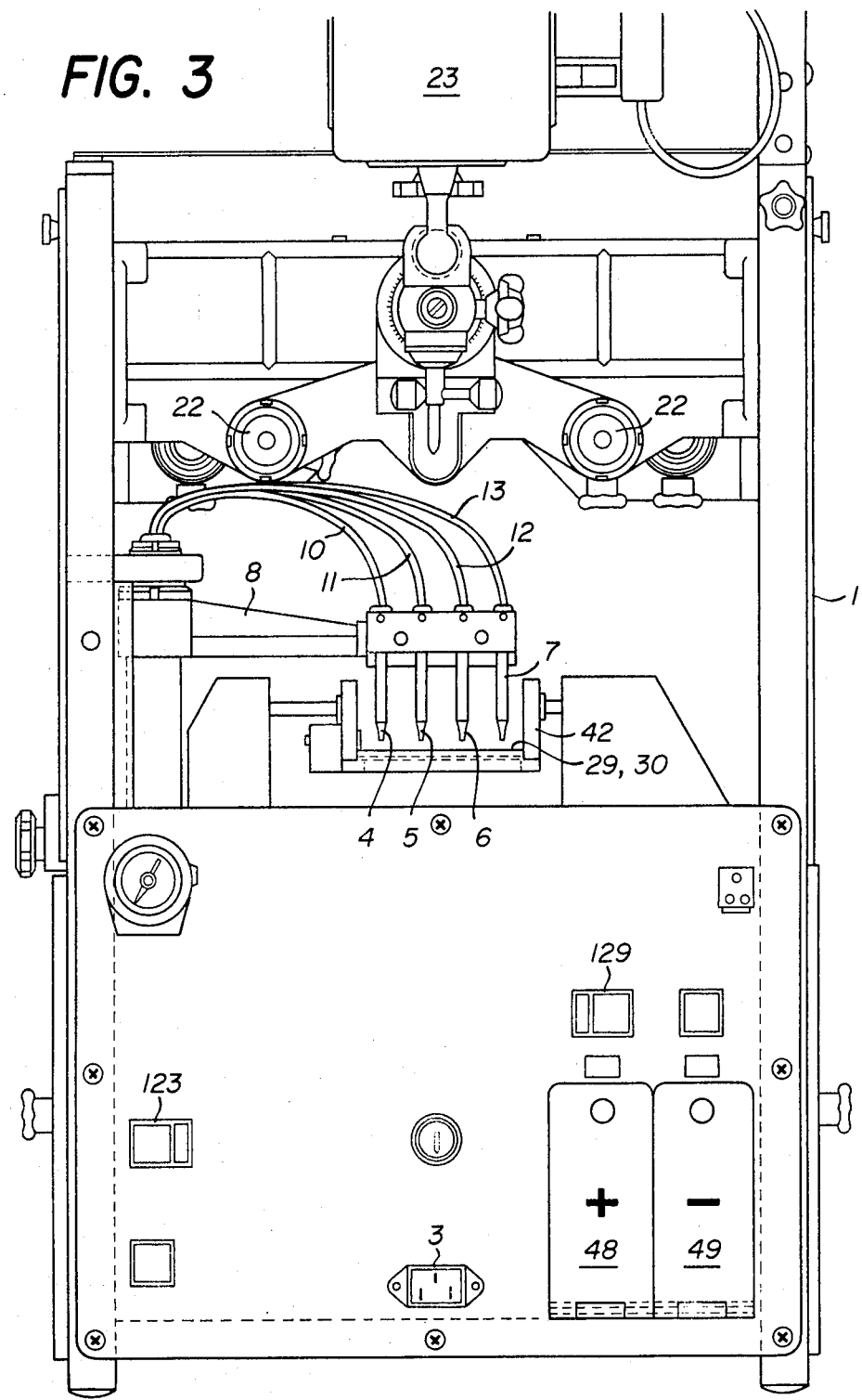
FIG. 3 is a view from the right, on an enlarged scale, of a part of the FIG. 1 installation.

As will be observed from FIG. 3, the installation also comprises two drawers 48 and 49 provided, one, with the + sign, the other with the − sign. Each of the drawers contains four transparent auxiliary plates 30 respectively provided with the markings A+, B+, AB+, O+, in the case of drawer 48, and A−, B−, AB− and O−, in the case of drawer 49.

Figure 4:
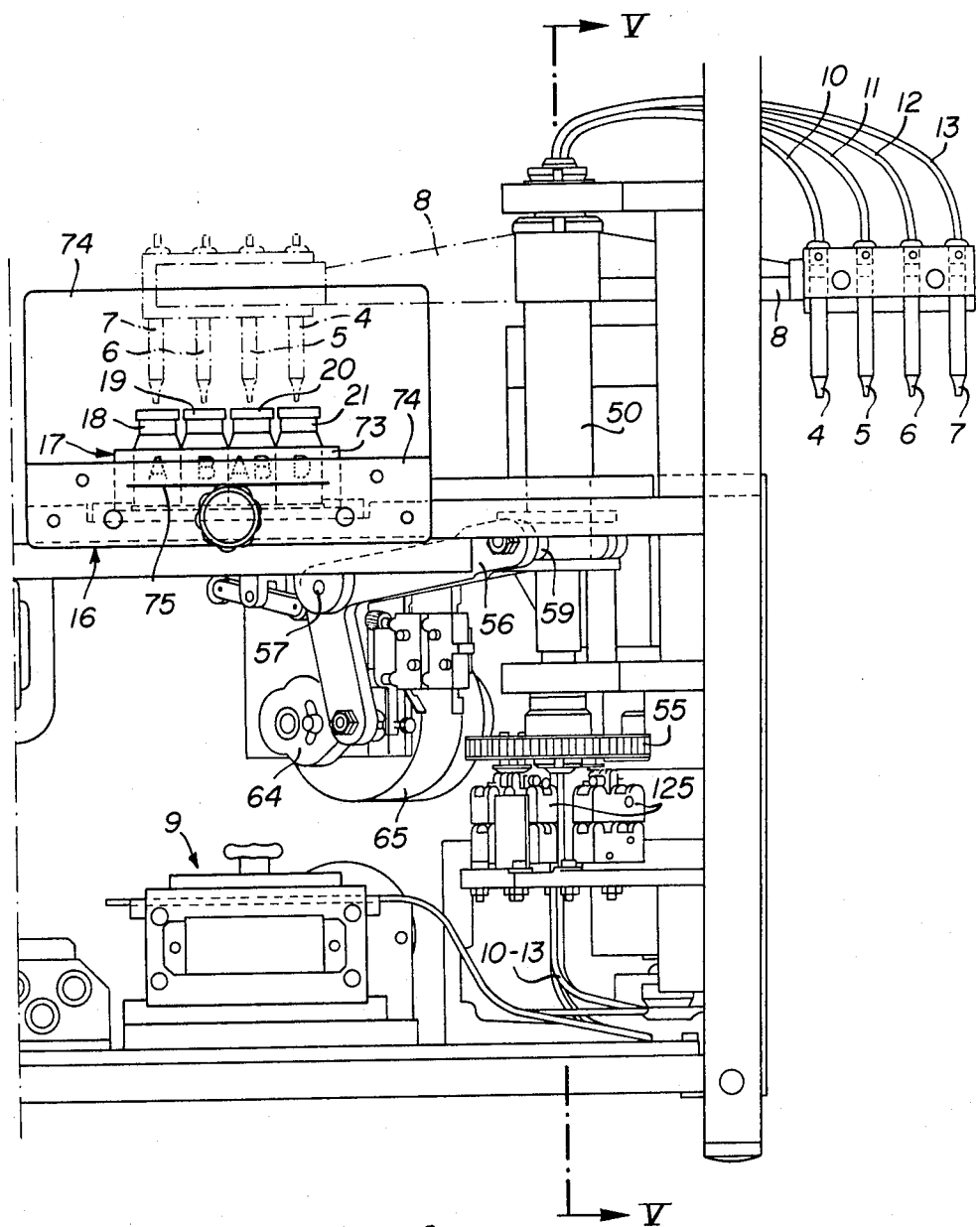
FIG. 4 is a partial view from the left of FIG. 3, after removal of a wall plate, showing a rotary pipette-carrying arm in an outer position.
Figure 5:
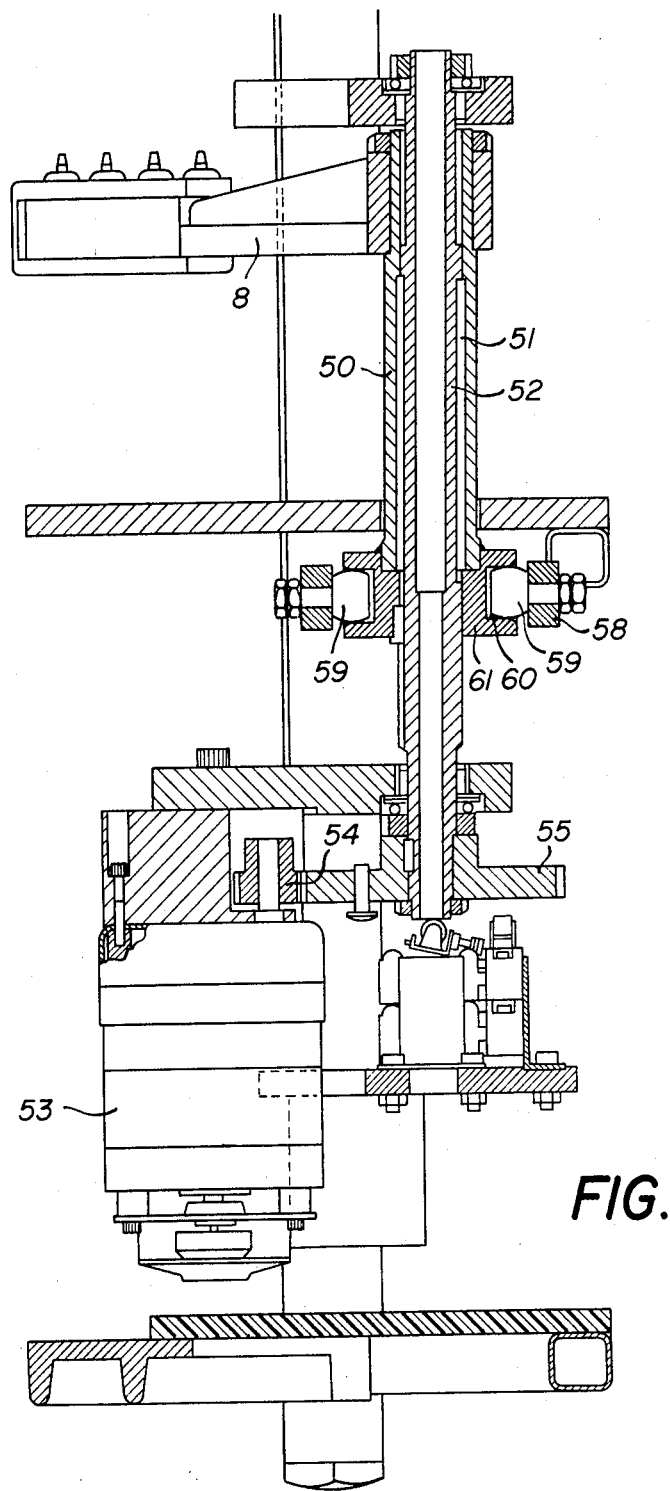
FIG. 5 is a section along line V—V of FIG. 4.

In FIGS. 4 and 5 is essentially shown the mechanism for rotating the movable arm 8 during an operative cycle. To this end, the arm 8 is rigid with a sleeve 50 that is internally fluted at 51 and mounted on a rotary shaft 52 having corresponding external flutes, whereby the sleeve 50 may move axially whilst being rotationally interlocked with the shaft 52.

Consequently, rotation of the shaft 52, by an electric motor cum brake 53 via pinions 54 and 55, enables angular motion of the arm 8 to move the pipettes 4, 5, 6 and 7 either over the serum bottles 21, 20, 19 and 18 respectively, or over the plate 29, or outside the casing 1, as shown in full lines in FIG. 4, to enable blood on the individual's finger to be taken up.

Axial movement of the sleeve 50, in particular to enable the pipettes to dip into the serum bottles, is brought about by a bell-crank lever 56 (see in particular FIGS. 8 and 9) that pivots at 57 and is provided, at one of its ends, with a fork 58 having a pair of rollers 59 lodged in an annular groove 60 of a member 61 (FIG. 5) rigid with the sleeve 50.

The lever 56 is provided at its other end 62 with a roller 62 which is applied to the periphery of a cam 64 mounted on the output shaft of an electric motor 65. The lever 56 has a heel 66 against which is applied a lever 67 that pivots at 68; it moreover cooperates with a stud 69 pushed by a spring 70. The spring thus acts on the lever 56 to permanently maintain the roller 63 in contact with the periphery of the cam 64.

The cam 64 thus causes by its rotation, in cooperation with the spring 70, the lever 56 to pivot and hence the sleeve 50 to move axially to lift or lower the pipettes 4, 5, 6 and 7.

Figure 6:
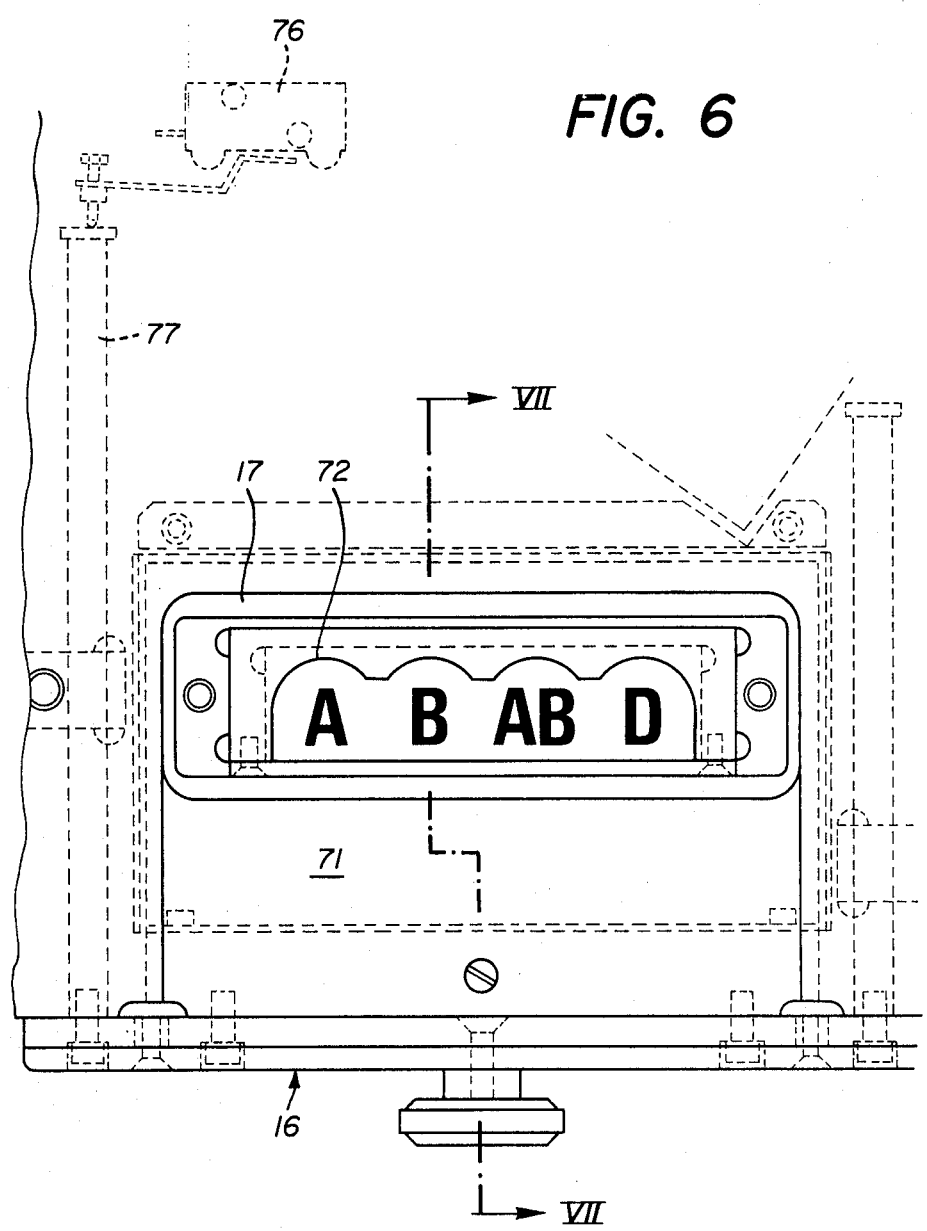
FIG. 6 is a view from above of a holder for test sera bottles, placed in the illustrated installation but without the bottles.

The drawer 16 that receives the serum bottles 18 to 21 is shown in detail in FIG. 6. This drawer comprises a bottom 71 to which is secured the holder 17 for the bottles of test sera. The holder 17 is formed with compartments 72 whose dimensions correspond substantially to those of the serum bottles. The base of this holder 17 is provided with markings A, B, AB and D, corresponding to the serum bottles, to facilitate their positioning.

To avoid any error in the positioning of the bottles in the holder 17, the letters A, B, AB and D of the test sera are applied to the bottles (see in particular FIG. 4), and on the front, transparent, wall 73 of holder 17 also. The wall 74 of the drawer 16 is also largely transparent. Thus, it is possible to check at any time whether a particular bottle of test serum is correctly placed in the holder 17. By providing a transparent front wall 74, it is also possible to check whether there is sufficient serum in the bottles by comparing the level of the serum with a reference line 75 also marked on the front wall 74 of holder 16. Moreover, to avoid inadvertent starting of the installation when the drawer 16 is not fully closed, a micro-switch 76 is provided so as to allow the installation to be supplied with electric current only when the micro-switch is actuated by a rod 77 of the drawer (FIG. 6).

Figure 8:
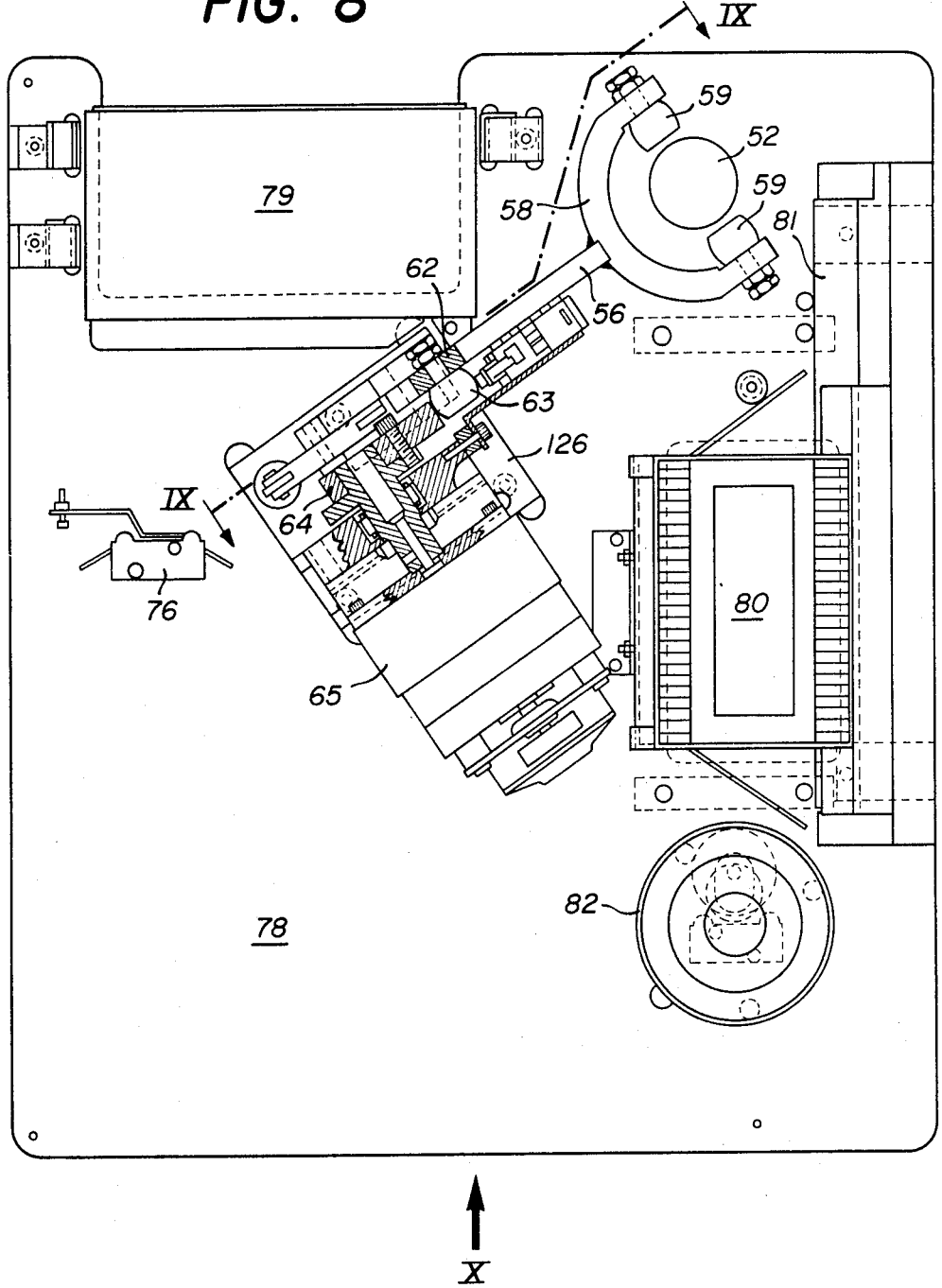
FIG. 8 is a view from below of part of the illustrated installation showing in particular a device for vertically actuating the pipette-carrying arm.
Figure 9:
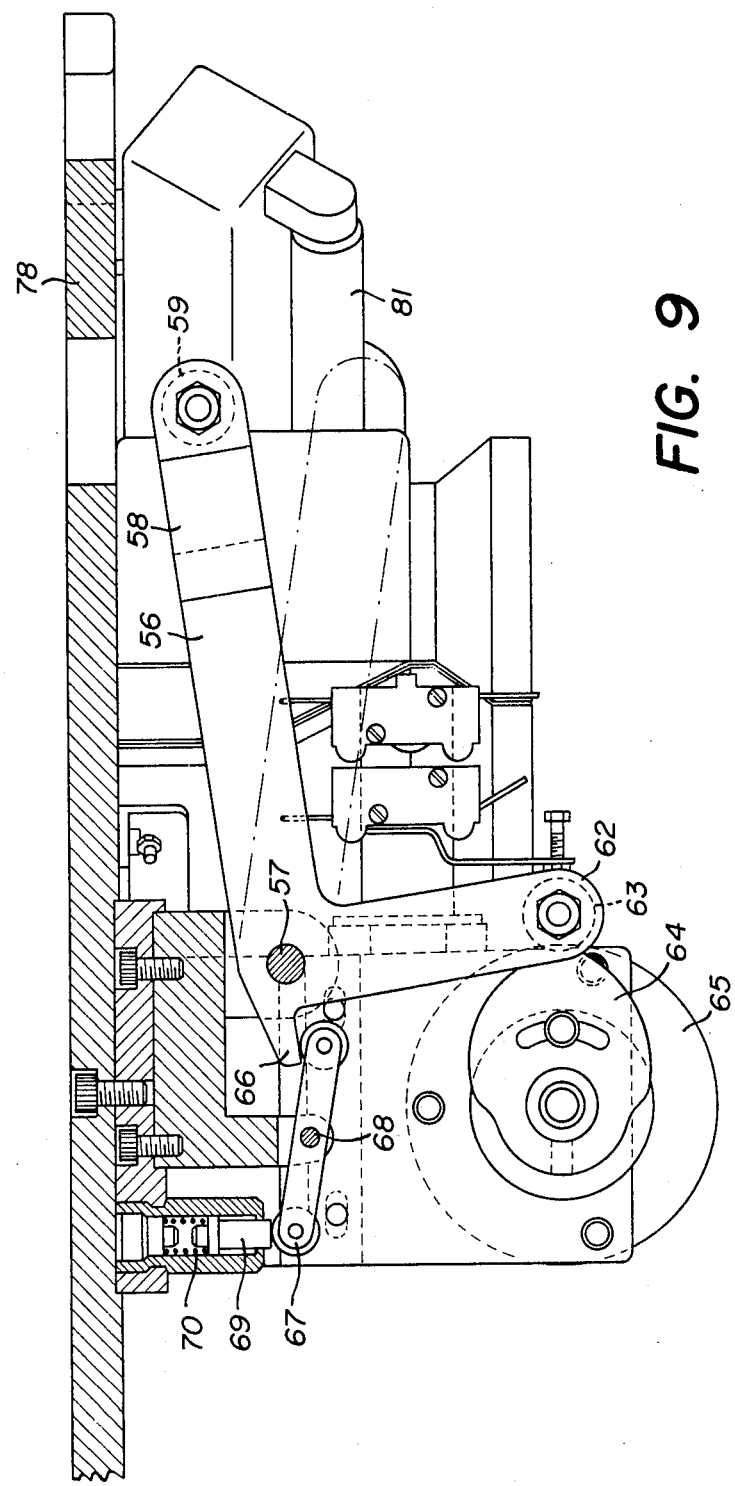
FIG. 9 is a section along line IX—IX of FIG. 8.

The motor 65 that controls the axial displacements of the sleeve 50 via lever 56 is secured to the underside of a plate 78 (FIGS. 8 and 9). The plate also carries the micro-switch 76, a support 79 on which slides the bottom 71 of drawer 16, and a lighting tube 81, and is formed with an opening 80 through which passes the light beam for the rear illumination of plates 29 and 30. On the underside of plate 78 is also secured an electric motor 82 whose output shaft 83 (FIG. 10) is fitted with an arm 84 carrying a crank pin 85. This pin slides in a sleeve 86 pivotally mounted at 87 on an arm 88 secured to the end of a shaft 89. The shaft 89 forms, together with a hollow shaft 90, a mounting means for the cradle 42. To this end, the shafts 89 and 90 are mounted in bearings in uprights 91 and 92 in such manner that they may move with a sliding and rotating motion. When the motor 82 is energized, rotation of the arm 84 causes the cradle 42, through the intermediary of sleeve 86, to move with a side to side motion and with a to and fro rocking motion. This construction thus enables the mixtures of test sera and blood deposited on the plate 29 to be agitated to produce the desired reactions under the most favourable conditions.

To stop the blobs of mixture from running into each other during agitation, ceramic strips are baked onto the top surface of plate 29 along its longitudinal edges and cross-wise to define four separate areas. These baked on ceramic strips also stop any liquid from infiltrating beneath them.

At one end of cradle 42 and particularly on the side thereof having to receive the mixture of blood and anti-D serum, there is provided a heating resistor 93 for raising the temperature of the agglutination plate to about 40° C., as is necessary. This resistor is supplied with electric current by a conductor 94 passing through the hollow shaft 90.

Figure 11:
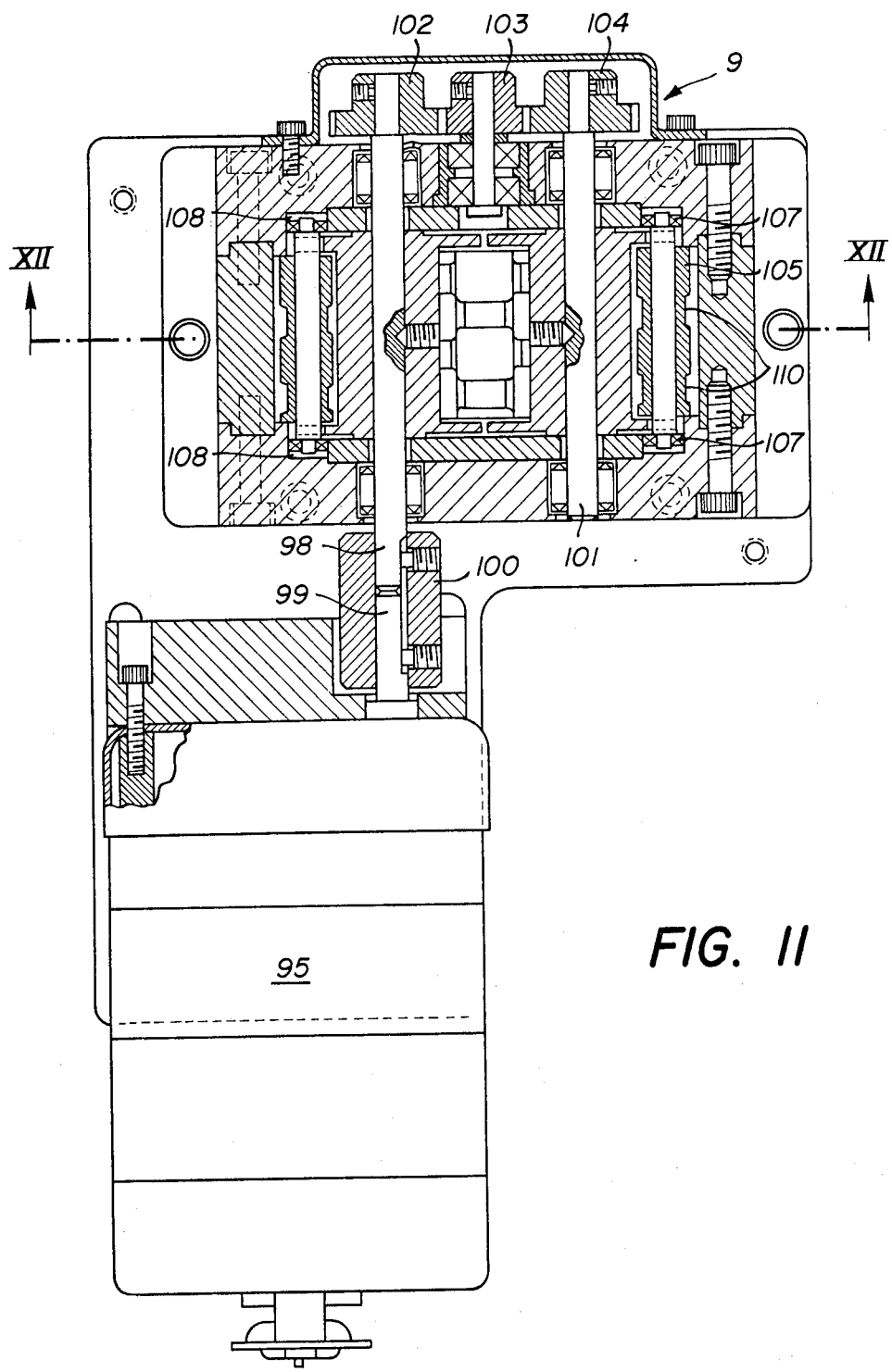
FIG. 11 is a partly sectional view of a peristaltic pump and motor unit comprised by the illustrated installation.
Figure 12:
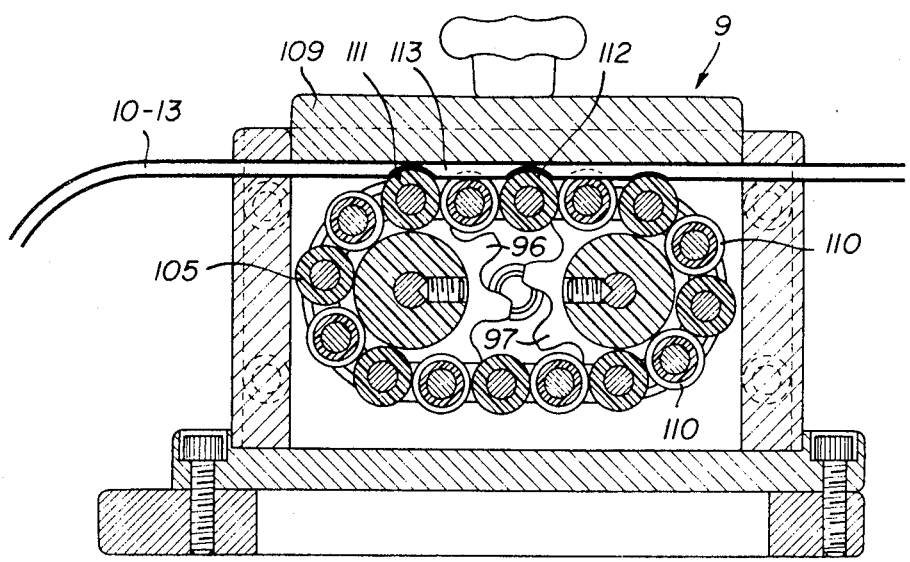
FIG. 12 is a section along line XII—XII of FIG. 11.

The sucking up of test serum and of blood into the pipettes 4, 5, 6 and 7 by the tubes 10, 11, 12 and 13 respectively and the discharge of the resulting mixtures is performed by the peristaltic pump 9 illustrated as a whole in FIG. 4 and in detail in FIGS. 11 and 12. This pump is designed so as to suck up and to discharge a constant quantity of test serum and/or blood so as to achieve optimum blood reaction conditions.

The peristaltic pump is driven by a motor 95 and comprises two cogged wheels 96 and 97 having a double set of involute teeth. Wheel 96 is driving and is connected to this end by its spindle 98, with which it is rigidly connected, to the output shaft 99 of motor 95 by a coupling sleeve 100. Wheel 97, which rotates in the same direction as wheel 96, is driven by its spindle 101, to which it is rigidly connected, off the spindle 98 via gearing comprising three pinions 102, 103 and 104, pinions 102 and 104 being secured to spindles 98 and 101 respectively. Between the two sets of teeth of wheels 96 and 97 is arranged a series of rollers 105. To enable them to roll on the tubes 10 to 13 without rubbing the latter, the rollers 105 are rotatably mounted on spindles 106 whose end portions are engaged by the double set of teeth on the wheels 96 and 97, while passing therearound, to move them forward. The end portions of spindles 106 are moreover provided, on the outside of the teeth of wheels 96 and 97, with ball bearings 107 arranged to roll in two elongated closed loop guideways 108 that include each at least one rectilinear section in the region of a wall 109, and parallel thereto, whereby the rollers 105 may move parallel to and at a small distance from this wall 109 thereby to nip between them in precise fashion the tubes 10 to 13 leading to the pipettes.

Each roller 105 is formed with two annular grooves 110 and the grooves of two consecutive rollers in a series are offset through inversion of the rollers whereby (FIG. 12) each tube may be nipped against the wall 102 by the periphery of at least two non directly adjacent rollers 105. Thus between each pair of non directly adjacent rollers, e.g. rollers 111 and 112, there may be formed in the tubes zones 113 having a constant volume of air capable of achieving the suction and discharge of a constant volume of serum and of blood by the pipettes 4 to 7.

Figure 7:
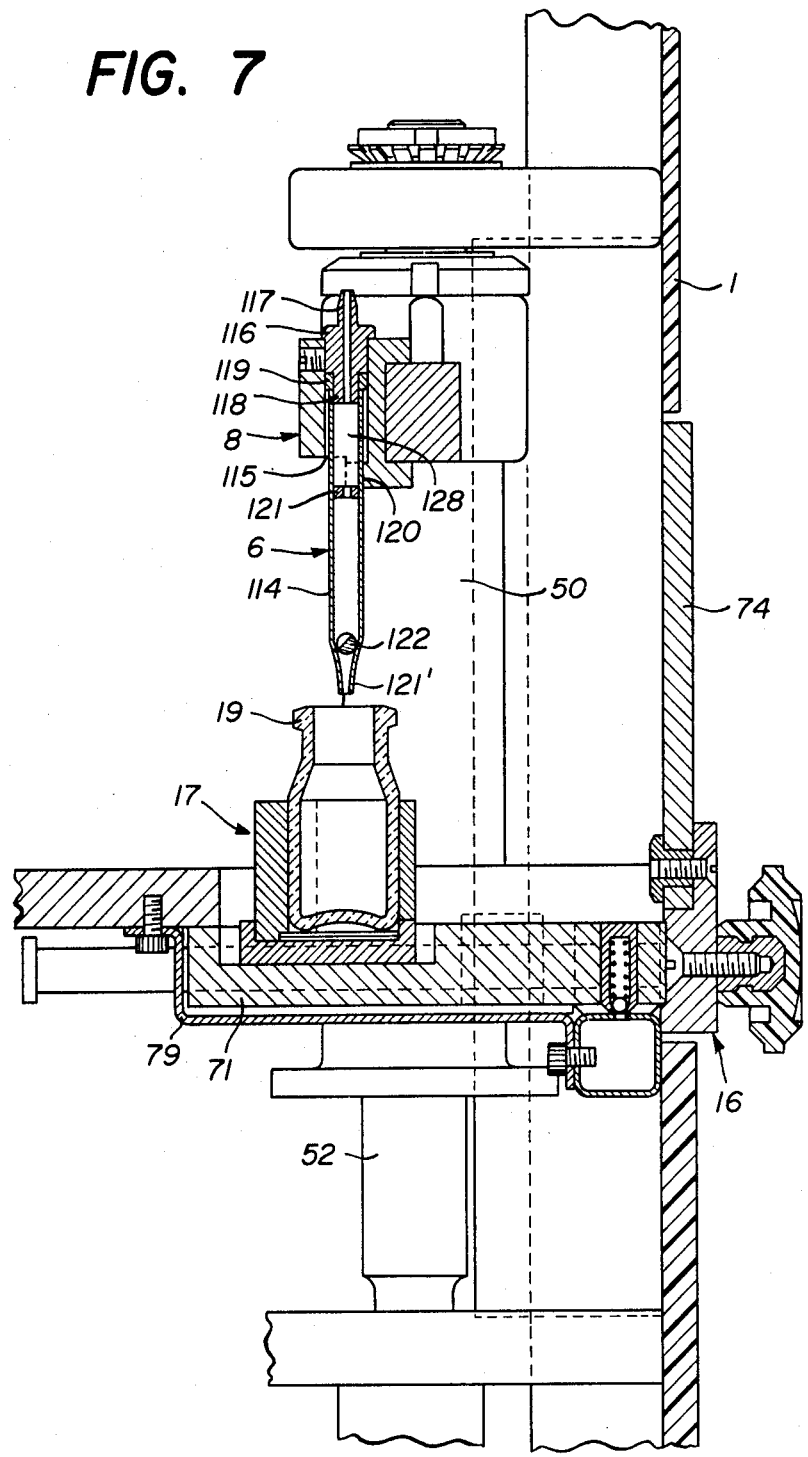
FIG. 7 is a section along line VII—VII of FIG. 6 but with the bottles and showing the rotary pipette-carrying arm with the pipettes positioned above the bottles.

The pipette 6, visible in FIG. 7 and identical to the other three, comprises a body 114 of plastics material removably fitted into a cylindrical cavity 115 which is formed in arm 8 and into the top of which is fluidtightly secured a member 116 having an axial passage therethrough. The top of member 116 is provided with a nipple 117 for connecting the tube 11 thereto (FIG. 4) and the lower end portion 118 of member 116 is of reduced diameter to define an annular groove into which may be inserted the top end portion of body 114. This top end portion is formed with an outer peripheral marginal bead 119 of rectangular cross-section so dimensioned that the top end of body 114 will closely fill the top of the annular groove and thus ensure a fluidtight fit of the body 114 on the male portion 118. The top of the annular groove moreover acts as a stop for correctly positioning the pipette heightwise. Inside the body, below the bead 119, is provided a fine circumferential inner bead of substantially triangular cross-section (not shown) which surrounds and presses against the male portion 118. In so doing, the wall of body 114, whose internal diameter corresponds to the diameter of male portion 118, is slightly distended thereby improving the seal of the pipette 6 in arm 8. This arrangement also enables rapid fitting and removal of the pipette, which is replaced after each use. The bottom of the front portion of arm 8 is higher than the bottom of the rear portion, thereby facilitating the insertion of the pipettes, and the lower rear portion of arm 8 is formed with semi-circular bearing surfaces 120 having the same diameter as the outer diameter of body 114, to ensure correct vertical positioning of the pipettes once inserted.

About half-way up the body 114 there is an annular element 121 having an internal diameter equal to the diameter of the passage through member 116. The lower end portion 114 narrows to define a spout 121' and, inside, a frusto-conical seat for a valve member 122 in the form of a slotted pellet having about the density of lead. Here, the valve member is a fishing line sinker with an irregular external surface.

The installation described so far operates as follows:

Before being started, the installation is adjusted by positioning the camera 23, the screen box 27 and the lighting device 25 by acting on the sliding tubes 22, 26 and 24. Also, the stop rods 28 are also adjusted so that the camera 23 may produce a sharp portrait of the person being examined.

By switching on the light source 46 and by acting on the lens unit 31, the sharpness of the projection of the plates 29 and 30 on to the screen 33 may be adjusted.

At the beginning of the operation, the installation is in the position shown in FIG. 1, i.e. the pipette-carrying arm 8 projects out of the casing 1.

Figure 10:
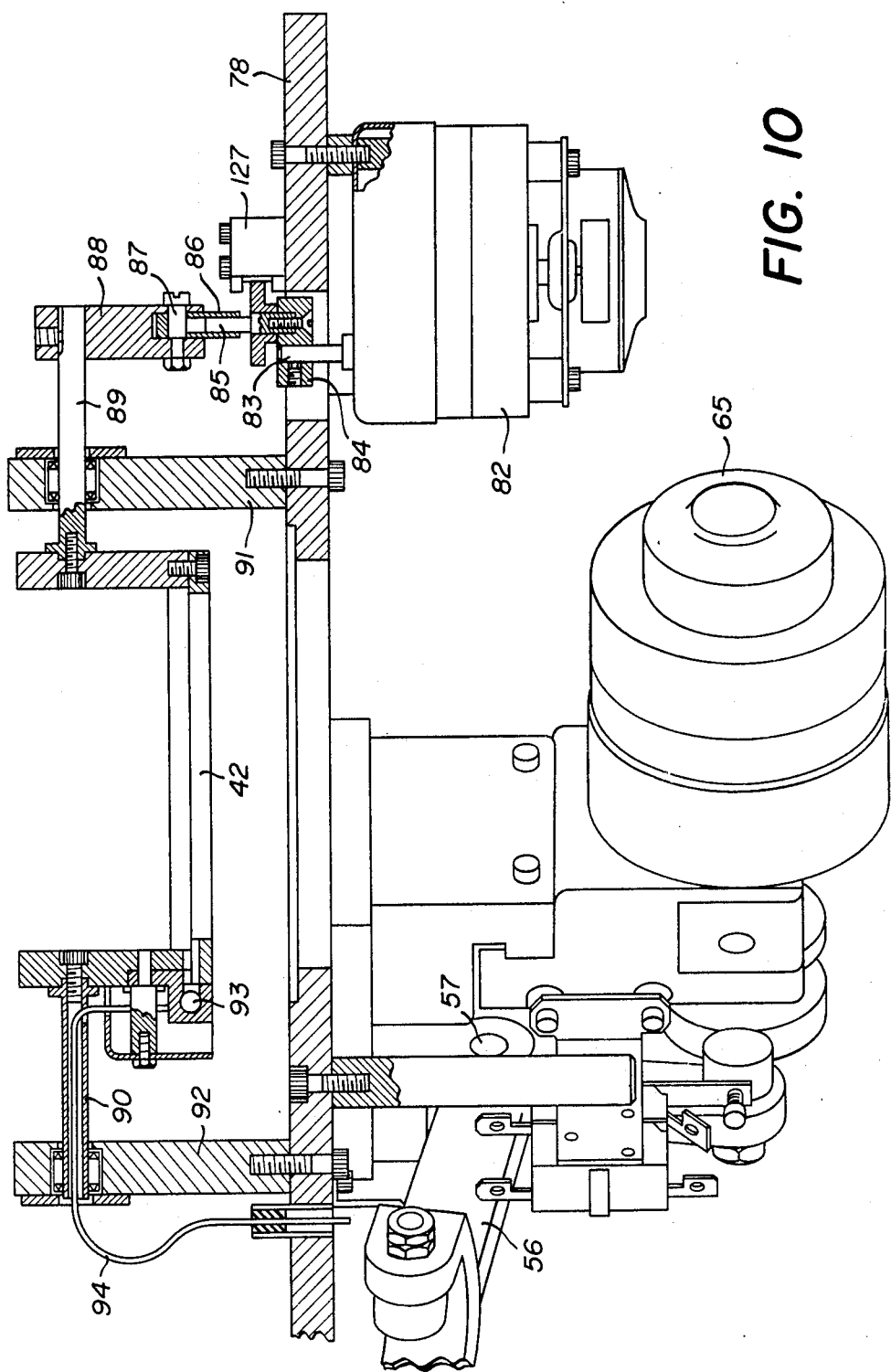
FIG. 10 is a view of FIG. 8 in the direction of arrow X, showing in particular a device for agitating an agglutination plate carrying cradle.

The installation is started by pressing a push button 123 (FIG. 3). Once started, the installation operates automatically in accordance with a cycle set by timing means 124 (FIG. 2) under the control of micro-switches such as 76 (FIG. 6), 125 (FIG. 4), 126 (FIG. 8) and 127 (FIG. 10). All of these micro-switches cooperate with movable parts of the installation to stop one part and to set in motion another.

Thus, on starting, the actuation of the push button 123 causes energization of the electric motor 53 which controls the rotary motion of arm 8 to move the pipettes vertically above the bottles 18 to 21. This horizontal rotational movement is ended by a micro-switch which also causes energization of the motor 65 to dip the lower ends of the pipettes into the serum of the bottles under the action of cam 64. Since the peristaltic pump 9 is operating, serum from each bottle is sucked into the associated pipette, whereupon the pipettes rise, still under the action of the cam 64 of motor 65. On reaching its uppermost position, arm 8 is again rotated, but in the opposite direction, through renewed energization of the motor 53 to move the pipettes outside the casing 1, as shown in FIG. 1.

The patient's finger having previously been asepticized and punctured with a vaccinostyle, blood is then successively sucked up into each of the pipettes that already contain anti-A, anti-B, anti-AB and anti-D test serum (anti-AB being the confirmation of A or of B). The motor 53 is again reenergized to reaction arm 8 and the pipettes above the agglutination plate 29. The rotational direction of the peristaltic pump is then reversed so as to discharge the sera and blood mixtures from the pipettes onto the plate 29. The motor 53 is then energized once again to cause the arm 8 to move outwardly.

During suction of the serum, the latter (which is metered by the time suction lasts) fills the spout 121' and covers the sinker 122, whereupon the pump 9 stops. During outward rotation of arm 8, the pump 9 is again started causing all of the serum to move above the sinker 122 before carrying out a blood sucking operation. The pump carries on operating and causes the blood to be sucked above the sinker 122 where it mixes with the serum, and the mixing forms rings which progressively rise up the wall of body 114, these rings being separated from each other by the pulsations of the pump. The rings accumulate beneath the annular element 121 which prevents them from moving into a compensation chamber 128, lying between the element 121 and the male portion 118, and beyond. The rings remain separate whilst moving closer. These rings ensure homogenization of the serum and blood mixture.

During discharge, the rings are repelled down the wall of body 114 by the air from the pump and accumulate in the region of sinker 122. Because of the slot and the irregularities on the surface of the sinker and under the action of the air pressure which overcomes the effects of capillarity occurring in the region of the slot and of the irregularities adjacent the wall of body 114 and preventing the liquid from flowing out through spout 121' when the pump stops, the liquid can be made to flow past the sinker 122 and be deposited on the plate 29.

When arm 8 has been moved away from plate 29 once the mixtures have been deposited, the agitating mechanism is set in motion by energizing the motor 82. After a set time, e.g. three minutes, the energization of this motor is interrupted by actuation of a micro-switch 127. The operator may then inspect the agglutination plate 29 and type the blood of the person being examined.

The operator then takes from one of the drawers 48 and 49, an auxiliary plate 30, corresponding to the analyzed blood group, and places this auxiliary plate 30 on the cradle 42 next to the agglutination plate 29. Error-avoiding means prevent faulty positioning of the latter.

At this stage of the operation, the flash 44 may be triggered simultaneously with the camera 23 to take photographs that each includes a portrait of the individual, a picture of the agglutination plate 29, a picture of the auxiliary plate 30, and a picture of the items of information about the person's identity previously put on the tablet 43.

As already indicated, the automatic cycle of operation of the installation is set by timing means and microswitches connected in an appropriate circuit such as to ensure the described operations being performed. If after a three-minute agitation, the reaction of the mixture of anti-D serum and blood is not sufficiently defined, additional agitation may be initiated, for a period of two minutes, by pressing on a push button 129 (FIG. 3).

In the two forms of checking apparatus illustrated in FIGS. 13 to 17, the same reference numerals are being used to designate equivalent parts.

Figure 13:
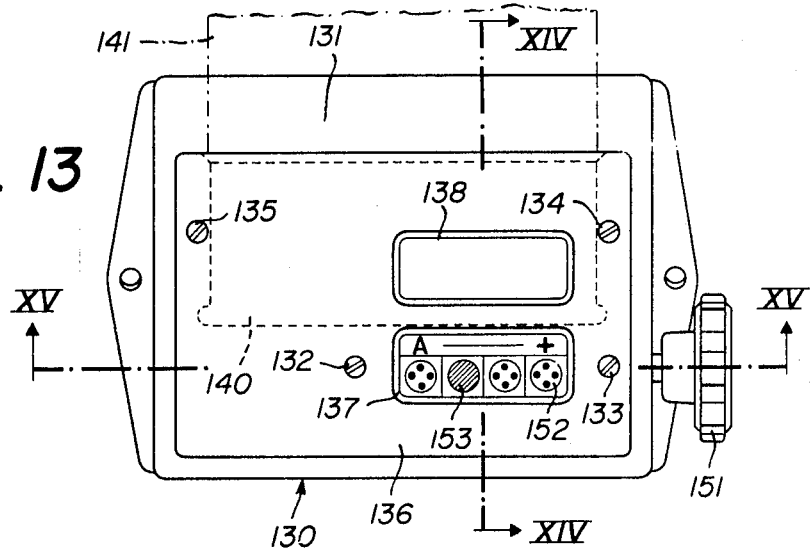
FIG. 13 is a front view of a first form of checking apparatus according to the invention for checking results obtained with the installation shown in FIGS. 1 to 12.
Figure 14:
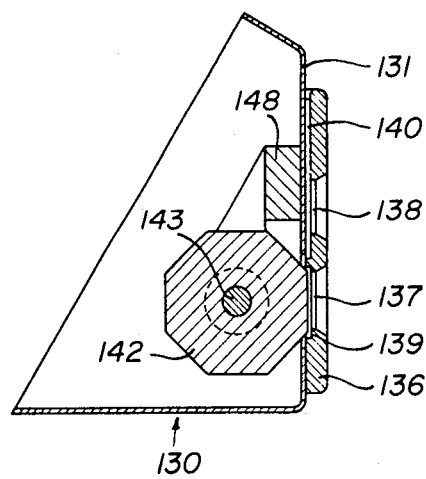
FIG. 14 is a section along line XIV—XIV of FIG. 13.
Figure 15:
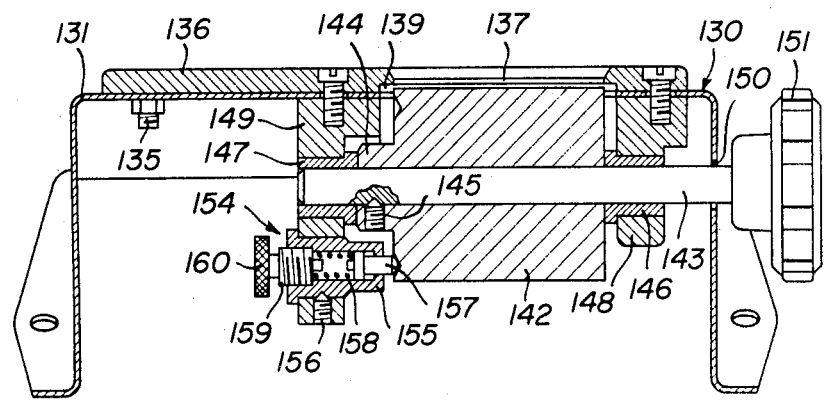
FIG. 15 is a section along line XV—XV of FIG. 13.

The apparatus illustrated in FIGS. 13 to 15 comprises a casing 130 intended to be secured by screws, not shown, to a wall such as one of the walls of the blood typing installation shown in FIG. 1.

The casing 130 has a front wall 131 to which is secured by screws 132, 133 and 134 and by a bolt 135 a plate 136 in which are formed two rectangular windows 137 and 138 disposed one above the other.

In the rear face of plate 136 are formed a rectangular recess 139 in which opens the window 137 and having dimensions slightly greater than those of this window, and a rectangular recess 140 in which opens the window 138 and whose dimensions are indicated by the broken lines visible in FIG. 13. The lower edge of the recess 140 is located at a small distance from the upper edge of the recess 139 and its upper edge is open, as is visible in FIG. 14, so as to define between the wall 131 and the plate 136 a slot in which may be inserted a record card 141 shown in ghost lines in FIG. 13.

Inside the casing 130 is mounted a member 142 having the shape of a regular eight sided prism. The member 142 has extending therethrough, along its axis, a shaft 143 and has at one of its ends an extension 144 through which extends radially a grub screw 145 for securing the member 142 to the shaft 143. The latter is rotatably supported in two smooth bearings 146 and 147 housed in bores made in two brackets 148 and 149 at opposite ends of the member 142 and secured to the inner face of the front wall 131 by screws 132 to 134. The shaft 143 extends beyond the bearing 146 and extends through an opening 150 made in one of the casing side walls to enable the member 142 to be rotated by means of a knurled control wheel 151 secured to the free end of the shaft. The bearings 146 and 147 define adjacent the member 142 abutment surfaces acting on the end walls of the member 142 and preventing any axial movement thereof.

The eight sides of the prismatic member 142 respectively bear eight sets of different data respectively made up, firstly, of the eight possible results, in graphical representation form, that one should be getting on an agglutination plate with four mixtures of blood, taken from the individual whose blood group and rhesus factor are to be determined, and of anti-A serum, anti-B serum, anti-AB serum and anti-D serum, and, secondly, of the corresponding conventional definitions, to wit A+, A−, B+, B−, AB+, AB−, O+ and O−.

The graphical representation adopted here for the eight possible results is that of red spots to indicate a state of non agglutination and reminiscent of the uniform aspect of a drop of mixture, on the plate, when the reaction has been negative, and that of white spots dotted with red reminiscent of the mottled aspect that a drop of mixture, on a plate, tends to have when the reaction has been positive. The spots 152 visible in FIG. 13 thus represent positive reactions and the spots 153 represent a negative reaction.

The eight possible results that one should be able to get with the above mentioned test sera are given in the following table, to which has been added, on the left, the conventional definition for each result.

| Conv. | SERUM ANTI | | | |
| def. | A | B | AB | D |
|---|---|---|---|---|
| A+ | P | N | P | P |
| A− | P | N | P | N |
| B+ | N | P | P | P |
| B− | N | P | P | N |
| AB+ | P | P | P | P |
| AB− | P | P | P | N |
| O+ | N | N | N | P |
| O− | N | N | N | N |

In the above table, P represents a positive reaction (agglutination) and N represents a negative reaction (non-agglutination).

If the data appearing in window 137 in FIG. 13 is compared with the data in the table, it will be observed (disregarding the fact that different symbols are used) that the data in that window corresponds, on the one hand, in all respects to the data in the first line of results in the table, the order adopted for the test sera being the same, and, on the other hand, from the conventional definition point of view.

The eight different sets of data borne by the member 142 act as reference data for checking the concordance of corresponding data appearing on record cards, such as record card 141, the latter data consisting of a reproduction of the results obtained on an agglutination plate and of a conventional blood group definition made by a laboratory assistant or other person with the potential for error that this involves. Clearly there must be concordance between the location of this data on the record cards and the location of window 138 in the apparatus.

In the present instance the illustrated apparatus has been designed to check record cards consisting each of four identical colour photographs, taken simultaneously and occupying the four quadrants of the card, each photograph comprising from top to bottom the portrait of the individual whose blood has been typed, his name, the conventional definition of his blood group and the results of the analysis in the form of a reproduction, by optical means, of the actual results obtained on the agglutination plate with the aid of an installation of the kind set forth earlier. Since the potential for error with this kind of installation is essentially limited to the conventional definition of the blood group and since the four photographs are identical, it suffices to check the last two items of information on one of the photographs, in this instance that occupying the lower right-hand quadrant of the card.

In carrying out a check, after having placed the record to be checked in the slot 140, one rotates the prismatic member 142 by means of the wheel 151 until there appears in the window 137 the same conventional definition as that shown in window 138 and one compares the photographic reproduction, visible in window 138, of the test results obtained on the agglutination plate with the graphic representation that can be seen in window 137. Alternatively, one rotates the prismatic member 142 until there appears in the window 137 the graphical representation corresponding to the results obtained on the plate, visible in the form of a photographic reproduction in window 138, and one checks to see whether the conventional definition visible in window 138 agrees with that visible in window 137. If there is concordance, the record card can be handed to the individual whose blood has been tested, and in the absence of concordance, thereby indicating the existence of an error, the test is repeated.

To ensure that only the information of one set of data appears in window 137, rather than the results portion of one set and the definition portion of another set, a problem that has already partly been resolved by the adoption of a data carrier of prismatic shape, there is also provided an indexing mechanism 154 comprising a hollow body 155 secured by a grub screw 156 in a bore made in the bracket 149, and in which may slide a pointed element 157 urged towards the member 142 by a spring 158 whose pressure can be adjusted by a threaded element 159 axially movable in the body 155 by means of a knurled head 160. The point of element 157 cooperates with eight regularly spaced cavities formed in the adjacent end face of member 142, these cavities being so positioned that when the point of element 157 is engaged in one of them, one of the sides of the prismatic body is in register with the window 137.

Figure 16:
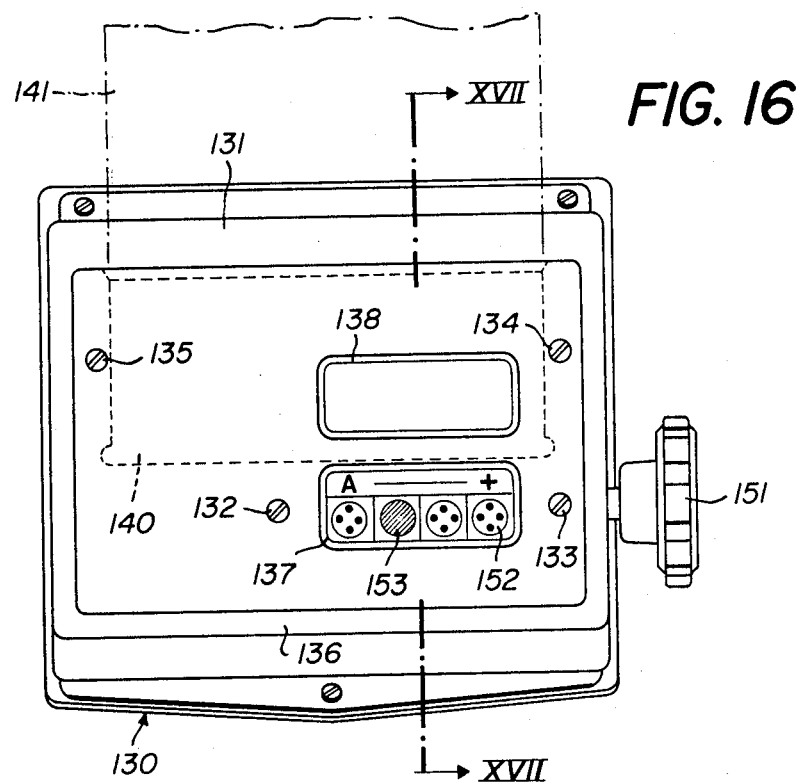
FIG. 16 is a front view of a second form of checking apparatus according to the invention for checking results obtained with the installation shown in FIGS. 1 to 12.
Figure 17:
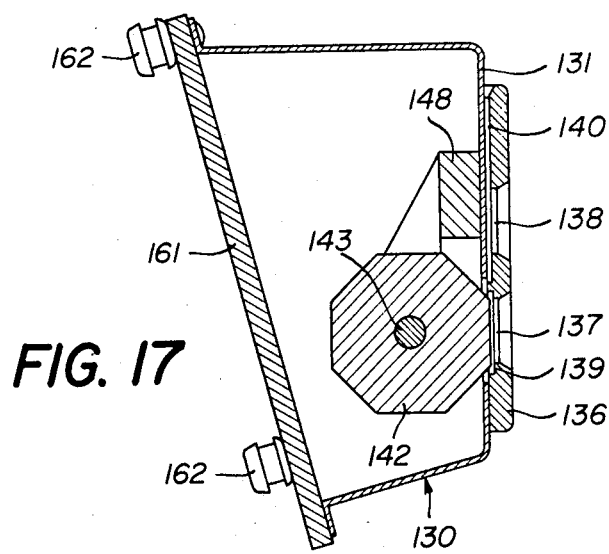
FIG. 17 is a sectional view along line XVII—XVII of FIG. 16.

The apparatus illustrated in FIGS. 13 to 15 is essentially meant for use at the test location. That shown in FIGS. 16 and 17 is essentially intended for use at another location, e.g. for additional checking purposes by a person having to certify the correctness of the data appearing on a record card. This second apparatus is in all respects similar to the first, except that it has been designed to be placed on a desk or other horizontal surface and its casing 130 has accordingly a slightly modified shape, the latter being additionally provided with a bottom 161 to which are secured rubber pads 162.

Clearly, the two forms of apparatus illustrated in FIGS. 13 to 17 and described by way of non limitative examples may be modified in various ways. For instance, the member 142 could be cylindrical and the windows 137 and 138 could occupy other positions depending on the location of the data to be checked on the cards.

The bottle-holding device shown in FIGS. 18 to 21 comprises a holder 163 containing a row of four bottles 164, 165, 166 and 167. The holder 163 is, viewed in plan, of oblong rectangular shape and has a bottom 168, end walls 169 and 170, a rear wall 171 that is integral with the end walls 169 and 170, and a front wall 172 of transparent material, e.g. glass. The various components of the holder 163 are secured to one another by glue, screws or the like to form a rigid assembly intended to be removably placed in a base plate 173 permanently secured as by screws 174 and 175 in a blood typing installation such as that illustrated in FIGS. 1 to 12.

To ensure that the holder 163 is correctly positioned in the base plate 173, firstly an oblong rectangular recess 176, in which the holder 163 may be placed, is formed in the top face of the base plate 173 and secondly an upright spigot 177 is disposed near one end of the recess 176 so as to be capped by a coinciding recessed hole 178 formed in the base of wall 169.

Figure 18:
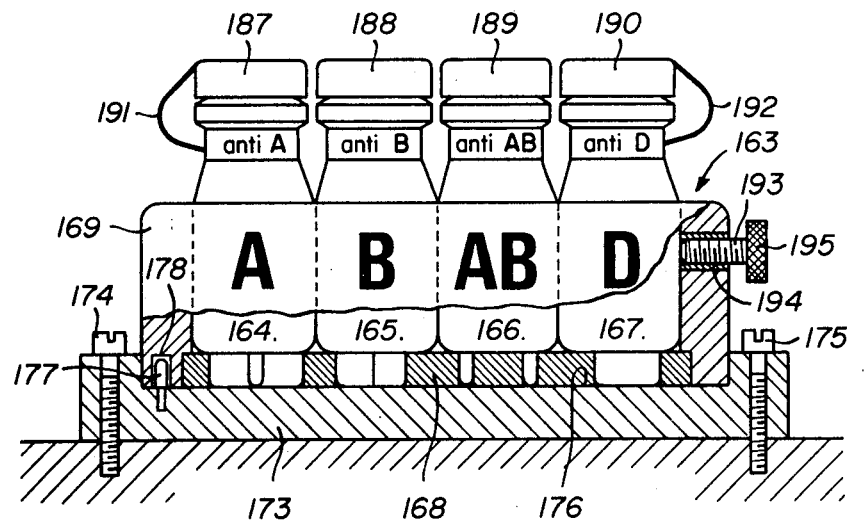
FIG. 18 is an elevational view partly in section of a bottle-holding device according to the invention, shown in position in a blood typing installation similar to that shown in FIGS. 1 to 12.

The necks of bottles 164 to 167 are surrounded by coloured, respectively, green, red, blue and white, bands which moreover bear, respectively, the markings "anti-A", "anti-B", "anti-AB" and "anti-D", corresponding to the test sera contained in the bottles. The latter are arranged in the holder in a set order to enable the various operations carried out by the blood typing installation in which the holder 163 is to be placed, to be correctly performed. To ensure correct positioning of the bottles in the holder 163, the bottles have on their bottoms projections 179, 180, 181 and 182 of different configurations, as may be seen in FIG. 19, and which are inserted into cavities 183, 184, 185 and 186 of corresponding configurations formed in the bottoms 168 of holder 163, as shown in FIG. 20. To facilitate rapid placing of the bottles in the holder without having to consider elements 179 to 186, letters A, B, AB and D are engraved in the rear face of the transparent front wall 172, as shown in FIG. 18, to designate to the person placing the bottles in the holder the positions they have to occupy in the latter, by referring to the markings on the bands surrounding the bottle necks. Thus, the bottle bearing the marking "anti-A" is inserted in the holder 163 at the location marked A, the bottle bearing the marking "anti-B" is inserted in the holder 163 at the location marked B, and so forth. To facilitate the placing of the bottles still further, the colours used on the bands of bottles 164 to 167 are correspondingly used to colour the engraved letters A, B, AB and D. There is thus a double indexing system for the placing of the bottles. If, despite this double indexing system, a bottle should still be wrongly inserted in the holder, the error would not be unnoticed since the projection on the bottle could not be inserted in the cavity of that location. As an additional precaution, the bottles 164 to 167 are provided with stoppers 187, 188, 189 and 190 that are connected to the coloured bands surrounding the bottle necks by strips like those shown at 191 and 192 in FIG. 18. Thus, no mixing of the test sera can occur through inadvertent switching of the stoppers.

The side wall 170 of the holder 163 is moreover provided with a screw 193 cooperating with a part 194, having a threaded hole, set in the wall. The screw 193 has a milled head 195 that can be hand operated to press the bottles 164 to 167, once placed in the holder, against each other and against the wall 169. The bottles cannot thus be removed from the holder without first being released, nor drop out during handling of the holder.

Figure 19:
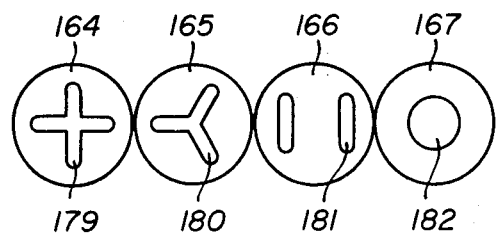
FIG. 19 is a view from below of the bottles visible in FIG. 18.
Figure 20:
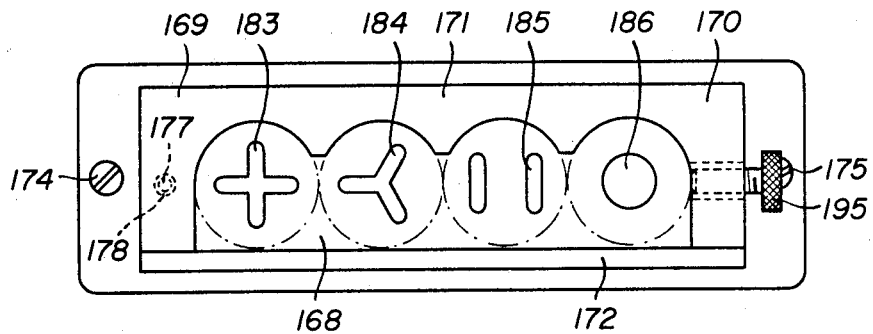
FIG. 20 is a plan view of the device shown in FIG. 18 without the bottles.

Various modifications may be made to the form of embodiment described and illustrated by way of example in FIGS. 18 to 20. For instance, instead of the spigot 177, any other system that only allows one locating position of the holder 163 in the base plate 173 may be adopted, e.g. one of the rear corners of the recess 176 and of the holder 163 may be rounded. The various locations on the bottom 168 could also be coloured in accordance with the colours used on the bottles and the wall 170.

Figure 21:
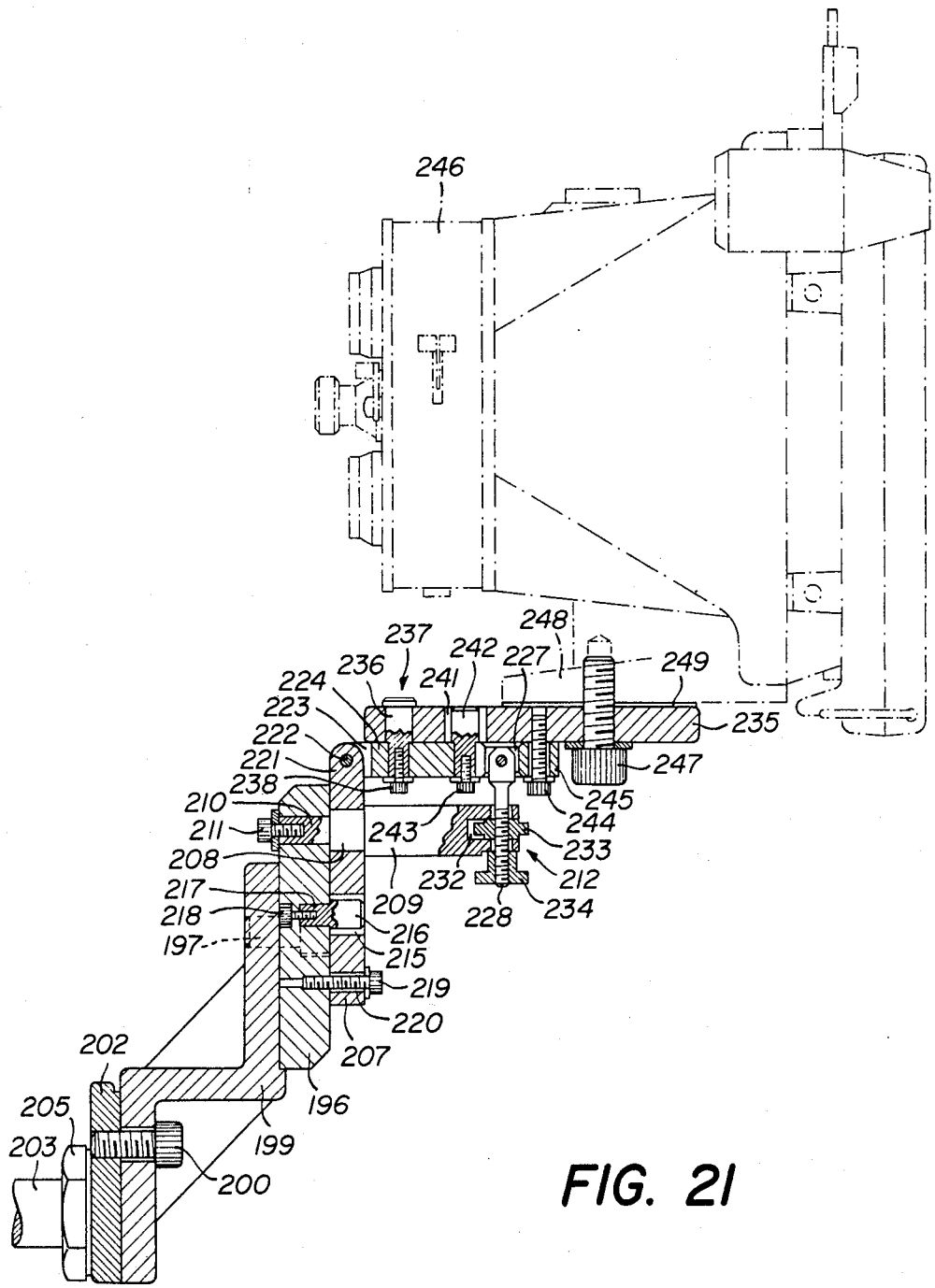
FIG. 21 is a sectional side view of an adjustable mounting according to the invention, capable of use in the installation shown in FIGS. 1 to 12 and shown carrying a camera in ghost lines.

The mounting shown in FIGS. 21 to 23 comprises a base plate 196 secured by screws 197 and 198 to an adapter member 199 which is in turn secured by screws 200 and 201 to the middle of a plate 202 whose end portions are secured to the ends of two sliding rods 203 and 204 by nuts 205 and 206.

The heads of screws 197 and 198 are countersunk in the base plate 196 to enable one of the faces of a generally T-shaped plate 207 to bear against the front face of the latter. The plate 207 is rotatably mounted on a journal 208 provided between a shank 209 of greater diameter and a stud 210 of lesser diameter which is inserted into a corresponding smooth hole extending through the upper portion of the base plate 196 and in which it is retained by a screw 211 passing through a washer bearing on the rear face of plate 207. The elements 208, 209 and 210 together constitute an integral member 212 that fulfils the double function of a pivot and of a milled wheel holder as will be described further on.

The plate 207 may be moved angularly on the journal 208 by means of two grub teat-screws 213 and 214 disposed opposite one another in the narrower portion of plate 207, their teats opening into a smooth circular hole 215 formed in the plate 207 and bearing on opposite sides of a buffer 216 of circular cross-section having a smaller diameter than the hole 215. The buffer 216 has a stud 217 that is inserted into a smooth recessed hole in which it is retained by a screw 218 whose head is countersunk in the rear face of plate 207 so as not to interfere with the angular movements of the latter.

If it is desired to rotate the plate 207 clockwise through a certain angular distance (FIG. 22), e.g. to move the axis of symmetry of the plate into the vertical position, one releases the screw 214 to a sufficient extent, one turns the screw 213 by the required amount and one tightens again screw 214.

To immobilize the plate 207 in this new set position, there is further provided a locking screw 219 which extends through a smooth hole 220 formed in the lower portion of plate 207, and whose head bears against the front face of the latter via a washer. The hole 220 is of arcuate or elongated cross-section to enable the angular adjustments of plate 207 to be carried out.

The upper edge of the plate 207 is formed with a central lug 221 on which is hinged by a pin 222 a fork 223 of a substantially horizontal plate 224. The pin 222 is held in place by two grub teat-screws 225 and 226 that are inserted into partly threaded holes formed in the limbs of the fork 223.

Through the plate 224 extends a smooth hole 227 in which is pivotably mounted an eye bolt 228 through whose eye extends a pin 229 held in place by two grub teat-screws 230 and 231, as with the pin 222. The eye bolt 228 passes with substantial clearance through a smooth diametral hole which is formed in the free end of the shank 209 of member 212 and which is interrupted half-way along by an open perpendicular slot 232 in which is disposed a milled wheel 233 formed with a central threaded hole through which extends the bolt 228, the latter moreover bearing on its free end a milled locking nut 234 cooperating with a flat on the cylindrical surface of shank 209. The slot 232 and the milled wheel 233 are sized to permit free rotation of the latter without any axial play. Thus, by releasing the locking nut 234 and by turning the milled wheel 233 in one or other direction the angular position of plate 224 can be accurately adjusted in relation to plate 207. On completion of this adjustment, the nut 234 is again tightened against its flat to lock the plate 224 in its new angular position.

On the top face of plate 224 lies a plate 235 having the general shape of a table tennis bat. The plate 235 is rotatably mounted by its "handle" portion, on a journal 236 of a pivot 237 that further comprises a retaining head of greater diameter and a stud of lesser diameter which is inserted into a corresponding smooth hole extending through the hinged end portion of plate 224 and in which it is retained by a screw 233 passing through a washer bearing on the bottom face of plate 224.

The plate 235 may be angularly moved on the journal 236 by means of two grub teat-screws 239 and 240 disposed opposite one another in the "handle" portion of plate 235, their teats opening into a smooth circular hole 241 formed in the middle of said "handle" portion and bearing on opposite sides of a buffer 242 of circular cross-section having a smaller diameter than the hole 241. The buffer 242 has a stud that is inserted into a smooth through hole in which it is retained by a screw 243 passing through a washer bearing on the bottom face of plate 224. In the "bat" portion of plate 235 is formed a threaded hole in which is screwed a locking screw 244 after passing it through a smooth hole 245, of arcuate or elongated cross-section, formed in plate 224, the head of screw 244 bearing against the bottom face of the latter via a washer.

This arrangement is similar to that described with respect to plate 207 and it operates in an analogous manner for carrying out fine adjustments of the angular position of plate 235, in a substantially horizontal plane, in relation to plate 224.

The plate 235, in FIG. 21, carries a camera 246 secured thereto by a screw 247 which extends through a smooth hole made in plate 235, in alignment with the other holes therein, and which is screwed into a threaded hole formed in the base 248 of the camera 246, the head of screw 247 bearing against the bottom face of plate 235, beyond the free end of plate 224, via a washer. To prevent any slipping between the plate 235 and the camera 246, a circular sheet 249 of rubber, cork or the like, is bonded to the top face of the "bat" portion of plate 235.

The mounting described and illustrated in FIGS. 21 to 23 enables adjustments to be made in three orthogonal planes with a much greater degree of accuracy than with, say, a ball and socket joint such as that visible in FIGS. 1 and 2 and has moreover the advantage of not having its adjustments upset by even the slightest impacts on the supported object, as tends to be the case with a ball and socket joint.

Various modifications may be made to the mounting described and illustrated in FIGS. 21 to 23 by way of example. For instance, the various studs could be threaded and be inserted into holes that are threaded instead of being smooth, thereby avoiding retaining screws. The locking screws 219 and 244 may be placed between, respectively, the journals 208 and 236 and the buffers 216 and 242, after moving the latter, or the journals 208 and 236 could be placed between their associated locking screws and buffers. The member 212 may be divided into two separate parts, one acting as a pivot only and the other acting solely as a milled wheel holder, although the "combined" arrangement is the preferred arrangement. A two-screw fixing system may be resorted to for the camera, thus avoiding any splitting problem between the latter and the plate 235 and of having to provide the anti-slip sheet 249 on plate 235.

Clearly, the clearances provided between the buffers 216 and 242 and the holes 215 and 241, between the eye of bolt 228 and the hole 227, and between the shank of bolt 228 and the hole through which it extends, and the cross-section of holes 220 and 245 are dependent on the angular motion it is desired to achieve, firstly, between the plate 207 and the base plate 196, secondly, between the plate 224 and the plate 207, and thirdly, between the plate 235 and the plate 224.

We claim:

1. An apparatus for typing blood characteristics of an individual and for producing a photographic record of the appearance of the individual and the typing results,
   a camera;
   means for positioning the individual in a predetermined location in the field of view of the camera;
   a housing;
   means for supporting the camera relative to said housing in a position to receive an image of the individual in said predetermined location;
   a projection screen and means for supporting said screen adjacent said predetermined location and in the field of view of said camera;
   a transparent agglutination plate having a plurality of agglutination zones;
   means for collecting and for depositing blood samples from said individual and test sera on said zones;
   a plate holder for holding said agglutination plate in said housing away from the field of view of said camera, said plate holder having means for letting light pass therethrough and through said supported plate; and
   optical means including a light source for passing light through said plate holder and said zones on said plate and for projecting an image of said zones of said agglutination plate onto said projection screen, whereby a photographic record of the typing results on said plate and the appearance of the individual can be simultaneously obtained.

2. An apparatus according to claim 1 wherein said means for collecting and depositing includes
   a plurality of pipettes;
   a plurality of serum containers supported on said housing; and
   means for supporting said pipettes and for sequentially moving said pipettes, as a group, to a first location to receive blood samples from the individual, to said serum containers to receive measured quantities of serum therefrom, and to said agglutination plate held by said plate holder to deposit mixed blood samples and serum in said zones, the number of said pipettes being equal to the number of said containers and said zones.

3. An apparatus according to claim 2 and further comprising
   means for agitating said agglutination plate for a predetermined interval of time.

4. An apparatus according to claim 3 wherein said means for agitating includes
   means for supporting said agglutination plate holder for reciprocating swinging motion;
   an electric motor;
   means for coupling said motor to said means for supporting so that energization of said motor reciprocates said plateholder; and
   timer means for energizing said motor for a predetermined interval.

5. An apparatus according to claim 2 wherein each of said pipettes includes an elongated tubular body, said body having at one end an outer peripheral bead and an inner circumferential bead axially spaced along said body from said outer bead.

6. An apparatus according to claim 2 wherein each of said pipettes includes an elongated tubular body having near one end means defining an internal tapering surface, and an imperfect valve member within said body and cooperating with said tapering surface, said surface providing a seat for the valve member.

7. An apparatus according to claim 6, wherein the valve member is a slotted pellet having an irregular outer surface.

8. An apparatus according to claim 7, wherein the valve member is a fishing line sinker.

9. An apparatus according to claim 2 wherein said serum containers are bottles and said housing includes a support for said containers comprising means defining a recess to receive four bottles, the recess having a bottom and side walls defining locations for the bottles and having indicia A, B, AB and D corresponding to the test sera.

10. An apparatus according to claim 2 and further comprising a peristaltic pump and flexible tube means for connecting said pump to said pipettes.

11. An apparatus according to claim 10, wherein said peristaltic pump is driven by a reversible electric motor.

12. An apparatus according to claim 10, wherein the peristaltic pump comprises two cogged wheels having involuted teeth, surrounded by an endless series of rollers, a section of said series being located parallel to and at a short distance from a wall whereby said rollers may nip the tubes against the wall, said section being such that the tubes, during operation, may be nipped by at least two rollers at any one time.

13. An apparatus according to claim 12, wherein said rollers have annular grooves, the grooves of said rollers being in quincunx.

14. An apparatus according to claim 10, wherein the pipettes are removably mounted on their support and at the end of the associated tube means.

15. An apparatus according to claim 14, wherein said means for supporting said pipettes comprises an arm rigidly mounted on an upright sleeve, said sleeve being movably mounted for axial motion on a rotary shaft.

16. An apparatus according to claim 15, wherein the rotary shaft is rotatably driven by an electric motor and the sleeve is axially actuated by a second electric motor via a pivotal lever.

17. An apparatus according to claim 16, wherein said second electric motor acts on the pivotal lever via a cam in cooperation with elastic return means.

18. An apparatus according to claim 1 and further comprising means for checking on a photographic record made by said camera and including a reproduction of the typing result and a blood group definition in conventional A, B, AB or O form followed by the sign + or −, whether or not the definition corresponds to said result, by comparing said reproduction and said definition with corresponding reference data acknowledged as being correct, said means comprising a carrier on which are represented reference data corresponding to the various possible results that can be obtained on said agglutination plate and, adjacent each representation of each result, the corresponding conventional definition.

19. An apparatus including checking means according to claim 18, wherein said carrier is a rotary member the checking means including a casing in which said member is mounted, said casing having a window in which only one set of reference data, consisting of one of said possible results and the corresponding conventional definition, can be displayed at the same time.

20. An apparatus including checking means according to claim 19, wherein said rotary member has a regular polygonal cross-section, each side of the member bearing a set of reference data.

21. An apparatus according to claim 19 and further comprising an indexing device cooperating with the rotary member and serving to maintain each set of reference data, moved before the window, in a set position in relation thereto.

22. An apparatus according to claim 19, wherein said casing includes means for receiving said photographic record, and a second window for the display of said reproduction and said definition on said photographic record, said second window being located adjacent the first window to facilitate the comparison of the data displayed therein.

23. An apparatus according to claim 22, wherein said receiving means comprises a record holding device arranged to position said reproduction and said definition before the second window.

24. An apparatus according to claim 2 including container positioning means wherein each of said containers comprises a bottle having a distinguishing shape integrally formed on and protruding from the bottom surface thereof, and said housing includes means for receiving a set of said bottles no two of which have the same distinguishing shape, said means for receiving having a bottom surface with means defining a plurality of recesses equal in number to the number of bottles in said set, said recesses being formed to receive said protruding distinguishing shapes, whereby said bottles are placeable in said means for receiving only in one predetermined arrangement.

25. An apparatus including a bottle holding device according to claim 24, wherein said means for receiving comprises a holder having two end walls at opposite ends of a row of bottles, one end wall having manual screw clamping means for clamping the bottles against each other and against the other end wall.

26. An apparatus including a bottle holding device according to claim 25 wherein each of said bottles is provided with a stopper connected by a binder to the neck of the associated bottle.

27. An apparatus including a bottle holding device according to claim 24, wherein the holder and the bottles are provided with indexing means to facilitate the placing of the bottles in said set order.

28. An apparatus according to claim 1 wherein said means for supporting said camera includes an adjustable mounting which comprises at least one pair of elements connected to one another by a cylindrical pivot arrangement, and screw adjustment means cooperating with each said pair of elements to adjust the angular position thereof.

29. An apparatus including an adjustable mounting according to claim 28, wherein each of the elements of one pair of elements has a flat surface, which surfaces are disposed in facing relationship and are connected by a hinge joint to permit movement relative to one another in the plane of their flat surfaces, and wherein the adjustment means comprise at least one screw mounted on one of the elements and a member mounted on the other element, on which the screw may act.

30. An apparatus including an adjustable mounting according to claim 29, wherein said member comprises a buffer fixedly attached to said other element and extending into a hole formed in the first element and into which project end portions of two screws screwed into the first element on opposite sides of a plane passing through the pivotal axis of the two elements and the middle of the buffer.

31. An apparatus according to claim 29, comprising a second pair pivotally connected to said one pair by a common element, the two elements of said second pair forming approximately a right angle between them and their adjustment means comprising a member rigidly mounted on one of the elements, a screw slidably extending at least partially through said member, said screw being pivotally mounted on the other element, and a nut engaged on said screw, said nut being disposed in a slot formed in said member.

32. An apparatus including an adjustable mounting according to claim 28, wherein the two elements of one pair are jointed by a flap joint and form between them approximately a right angle, and wherein the adjustment means comprises a member rigidly mounted on one of the elements, a screw slidably extending at least partially through said member, said screw being pivotally mounted on the other element, and a nut engaged on said screw, said nut being disposed in a slot formed in said member.

33. An apparatus according to claim 32 wherein the two elements of said one pair each form common elements with respective second and third pairs of elements, the elements of said second and third pairs each having a flat surface, which flat surfaces are connected by a hinge joint so as to move relatively to one another in the plane of their flat surfaces.

34. An apparatus according to claim 28, further comprising locking means associated with each said pair of elements to lock them after adjustment of their angular position.

35. An apparatus according to claim 1 wherein each of said pipettes includes an elongated tubular body, said body being divided into two chambers by an internal annular element fixedly attached to said body.

36. An apparatus according to claim 1 wherein
said means for supporting said screen includes support members projecting from said housing and slide members on said screen slidably engaging said support members to permit said screen to be moved relative to said housing;
said support members further including an extendable rod having an enlarged end portion movable toward and away from said housing to establish said predetermined location for the individual.

37. An apparatus according to claim 1 wherein said optical means includes
a lens unit mounted on said housing and directed toward said agglutination plate held by said plate holder to receive light therefrom, and
a mirror mounted on said housing for reflecting light from said lens unit toward said screen,
said light source being mounted on the opposite side of said plate holder from said lens unit to cause light passing through said plate holder and plate to form an image on said screen.

38. An apparatus according to claim 37 wherein said light source includes an electronic flash.

39. An apparatus according to claim 38 wherein said light source includes a lamp and reflector for producing an image on said screen for focusing the camera.

40. An apparatus according to claim 37 wherein said means for supporting said screen includes
a box having an open side opening toward said mirror and said camera, said screen being mounted in said open side near the bottom thereof.

41. An apparatus according to claim 40 wherein
said box includes a movable top wall locatable in a plane passing above said mirror and said camera.

42. An apparatus according to claim 1 wherein said plate holder includes transparent means for receiving information bearing indicia about blood type group, said optical means being adapted to project an image including said indicia on said screen.

43. An apparatus according to claim 1, comprising a second source of light, means for mounting the second source of light in a position to illuminate an individual placed behind the screen in said predetermined position, and means for shielding the screen from light from the second source.

* * * * *